(12) United States Patent
Wang et al.

(10) Patent No.: US 9,345,905 B2
(45) Date of Patent: May 24, 2016

(54) HETEROCYCLIC AMIDES COMPOUNDS WHICH ARE HDAC6 INHIBITORS AND USED AS ANTI-TUMORAL AGENTS

(71) Applicant: Nanjing Allgen Pharma Co. Ltd., Nanjing (CN)

(72) Inventors: Zhaoyin Wang, Kirkland (CA); Lianhai Li, Pierrefonds (CA)

(73) Assignee: NANJING ALLGEN PHARMA CO. LTD., Nanjing (CN)

(*) Notice: Subject to any disclaimer, the term of this patent is extended or adjusted under 35 U.S.C. 154(b) by 12 days.

(21) Appl. No.: 14/361,278

(22) PCT Filed: Nov. 29, 2012

(86) PCT No.: PCT/CA2012/001101
§ 371 (c)(1),
(2) Date: May 28, 2014

(87) PCT Pub. No.: WO2013/078544
PCT Pub. Date: Jun. 6, 2013

(65) Prior Publication Data
US 2014/0322229 A1     Oct. 30, 2014

Related U.S. Application Data

(60) Provisional application No. 61/629,827, filed on Nov. 29, 2011.

(51) Int. Cl.
| | | |
|---|---|---|
| *A61K 31/437* | (2006.01) | |
| *A61K 31/498* | (2006.01) | |
| *A61K 31/407* | (2006.01) | |
| *A61K 31/403* | (2006.01) | |
| *A61K 45/06* | (2006.01) | |
| *C07D 495/14* | (2006.01) | |
| *C07D 487/04* | (2006.01) | |
| *C07D 471/14* | (2006.01) | |
| *A61N 5/10* | (2006.01) | |
| *A61K 31/519* | (2006.01) | |
| *C07D 471/04* | (2006.01) | |
| *A61K 31/4985* | (2006.01) | |

(52) U.S. Cl.
CPC ............... *A61N 5/10* (2013.01); *A61K 31/403* (2013.01); *A61K 31/407* (2013.01); *A61K 31/437* (2013.01); *A61K 31/498* (2013.01); *A61K 31/4985* (2013.01); *A61K 31/519* (2013.01); *A61K 45/06* (2013.01); *C07D 471/04* (2013.01); *C07D 471/14* (2013.01); *C07D 487/04* (2013.01); *C07D 495/14* (2013.01)

(58) Field of Classification Search
CPC . A61K 31/437; A61K 31/498; A61K 31/407; A61K 31/403; A61K 45/06; C07D 495/14; C07D 487/04; C07D 471/14; A01N 5/10
See application file for complete search history.

(56) References Cited

FOREIGN PATENT DOCUMENTS

| CA | 2597193 A1 | 2/2009 |
|---|---|---|
| CA | 2760541 A1 | 11/2010 |
| CA | 2768466 A1 | 1/2011 |
| CA | 2760516 A1 | 2/2011 |

OTHER PUBLICATIONS

Mautino et al., 2009, caplus an 2009:710144.*
Craven et al., 2010, caplus an 2010:1316684.*
International Search Report corresponding to PCT/CA2012/001101 mailed Mar. 1, 2013 (4 pages).

* cited by examiner

*Primary Examiner* — Sun Jae Yoo
(74) *Attorney, Agent, or Firm* — Kilpatrick Townsend & Stockton LLP

(57) ABSTRACT

The present document describes compounds of Formula I, pharmaceutical compositions comprising the same as well as methods of treating diseases such as a cancer, neurological disease, neurodegenerative disorder, stroke, traumatic brain injury, parasitic infection, inflammation or an autoimmune disease with said compounds.

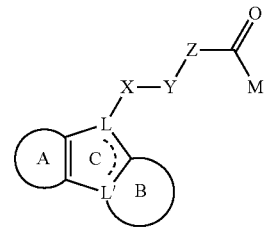

Formula I

11 Claims, No Drawings

HETEROCYCLIC AMIDES COMPOUNDS WHICH ARE HDAC6 INHIBITORS AND USED AS ANTI-TUMORAL AGENTS

CROSS-REFERENCE TO RELATED APPLICATIONS

This application claims priority of U.S. provisional patent application 61/629,827 filed on Nov. 29, 2011 the specification of which is hereby incorporated by reference.

BACKGROUND (a) Field

The present invention relates to novel amide compounds and their use as anti-tumoral and pro-apoptotic agents. The invention includes the use of such compounds in medicine, in relation to cancer disease, inflammatory diseases, neuronal diseases, parasite infections (e.g., *Plasmodium* infection), as well as other diseases where an inhibition of HDAC6 is responsive, and the pharmaceutical composition containing such compounds.

(b) Related Prior Art

Histone deacetylases have been biological targets of medicinal interest (see U.S. Pat. No. 7,250,504; U.S. Pat. No. 6,777,217; U.S. Published Application 20050287629). Post-translational modification of proteins through acetylation and deacetylation of lysine residues plays a critical role in regulating cellular functions. HDACs are zinc hydrolases that modulate gene expression through deacetylation of the N-acetyl-lysine residues of histone proteins and other transcriptional regulators. HDACs participate in cellular pathways that control cell shape and differentiation.

Vorinostat, originally known as SAHA (suberoylanilide hydroxamic acid), was the first-in-class small molecule hydroxamate derivative HDACi which has been approved by the FDA to treat a rare cancer, cutaneous T-cell lymphoma. SAHA is a potent non-selective HDACi inhibiting classes I and II as the vast majority of HDAC inhibitors currently in clinical trials.

Some clinical trials involving combination therapies have been conducted, to assess the efficacy of broad spectrum HDACi in combination with standard chemotherapeutic agents, (e.g., docetaxel and vorinostat), in patients with advanced and relapsed lung, bladder, or prostate cancer.

There is increasing evidence that HDAC6 plays a role in cancer cells and may be a target for drug development. HDAC6 presents the unique feature to possess two functional catalytic deacetylase domains and a carboxy terminal binding-of-ubiquitin zinc finger domain. Targeted inhibition of HDAC6 provokes acetylation of HSP90 and disruption of its chaperone function with its client proteins Bcr-Abl leading to antimetastatic and antiangiogenic effects, potential involvement of HDAC6 may also be potentially involved in the development of metastasis originating from breast cancer. HDAC6 inhibition has also been reported to be strongly involved in neuroprotection.

In summary, extensive evidence supports the potential for HDAC6 inhibitors in treatment of a variety of disorders and diseases, such as cancers and CNS diseases and degenerative conditions.

In the present invention, a novel series of heterocyclic compounds as potent HDAC6 inhibitors is disclosed, along with their potential uses as therapeutic agents.

SUMMARY

According to an embodiment, there is provided a compound of Formula I

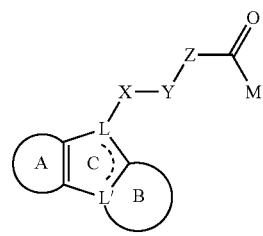

Formula I or a pharmaceutically acceptable salt thereof, wherein:

L and L' are selected from a nitrogen atom or carbon atom with the proviso that L and L' are a different atom;

X is O, S, $CH_2$, C(O), or a bond with the proviso that X is different than O and S when L is a nitrogen atom;

Y is a bond, an aryl, or a heteroaryl which is unsubstituted or substituted;

Z is a bond or selected from the groups consisting of $C_{1-8}$alkylene, $NR^a$, $C(O)C_{1-8}$alkylene, $C_{1-8}$alkyleneNRa, $C_{1-6}$alkylenearyleneC$_{1-6}$alkylene, $C_{2-8}$alkenylene, $C_{1-8}$alkylenearylene, $C_{1-6}$alkyleneheteroarylene, $C_{2-6}$alkenylenearyleneC$_{1-6}$alkylene;

any one of these groups being unsubstituted or substituted with one or more Ra;

M is selected from —NHOH, $CH_2SH$, $CH_2SC(O)C_{1-8}$alkyl, $CH_2SC(O)$aryl, $CH_2SC(O)$heteroaryl, $CH_2SC(O)C_{1-8}$alkylenearyl, $CH_2SC(O)C_{1-8}$alkylenheteroaryl or

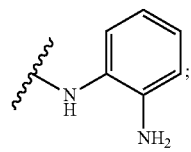 [SMILES: *Nc1ccccc1N]

wherein

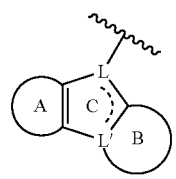

is selected from the following heterocyclic moieties:

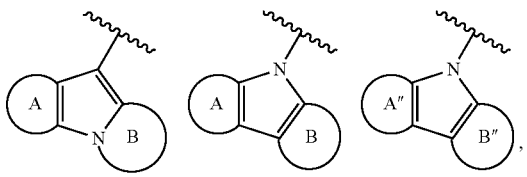

wherein

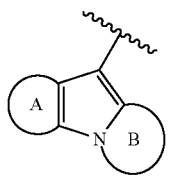

is selected from the following heterocyclic moieties:

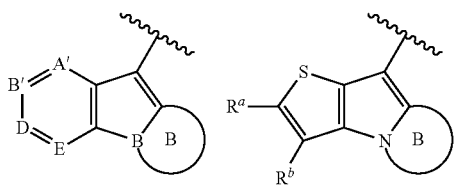

wherein each of A', B', D and E is independently selected from N, and C(R$^a$);
wherein, in

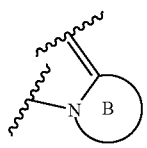

B ring is a 5 to 7-membered carbocyclic ring or a 5 to 7-membered carbocyclic ring in which one or more of the carbon atoms is replaced with C(O), O, S, NR$^c$, wherein R$^c$ is selected from hydrogen, C$_1$-C$_6$alkyl, C$_1$-C$_6$cycloalkyl, SO$_2$R$^e$, C(O)R$^e$,
wherein R$^e$ is C$_1$-C$_5$alkyl, C$_1$-C$_6$cycloalkyl, aryl, heterocycle, heteroaryl, with the proviso that there are no N—O or N—S bonds in B ring;
wherein

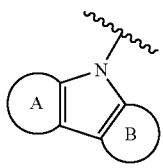

is selected from the following heterocyclic moieties:

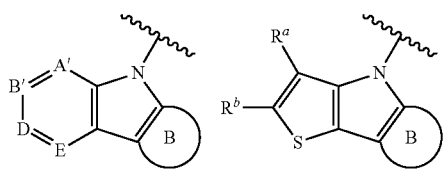

wherein each of A', B', D and E is independently selected from N, and C(R$^a$) with the proviso that at least one of A', B', C and D is N, wherein

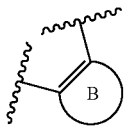

is a 5 to 7 membered carbocyclic ring or a 5 to 7 membered carbocyclic ring in which one or more of the carbon atoms is replaced with C(O), O, S, NR$^c$ wherein R$^c$ is selected from hydrogen, C$_1$-C$_5$alkyl, C$_1$-C$_6$cycloalkyl, aryl, heteroaryl, C$_1$-C$_6$alkylenearyl, C$_1$-C$_6$alkyleneheteroaryl, SO$_2$R$^e$, C(O)R$^e$.

wherein R$^e$ is C$_1$-C$_6$alkyl, C$_1$-C$_6$cycloalkyl, aryl, heterocycle, heteroaryl, C$_1$-C$_6$alkylenearyl, C$_1$-C$_6$alkyleneheteroaryl;
wherein

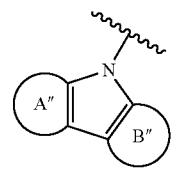

is selected from the following heterocyclic moieties:

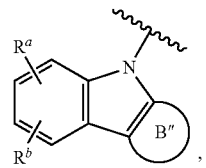

wherein
is selected from the following:

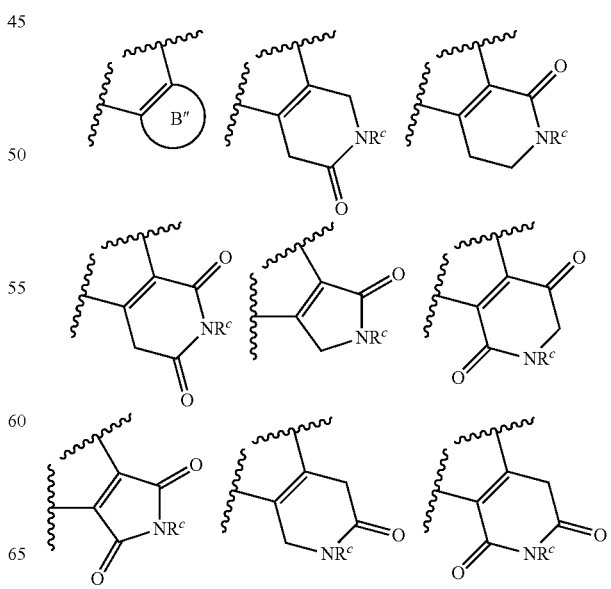

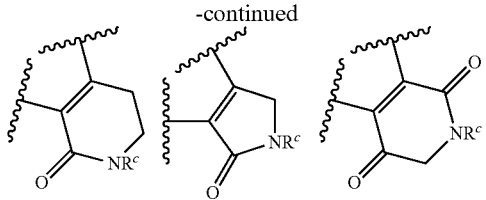

which are optionally substituted with one or more $R^a$ and $R^b$; $R^a$ and $R^b$ are independently selected from hydrogen, aliphatic, alicyclic, heteroaliphatic, heterocyclic, aromatic, heteroaromatic, aryl, heteroaryl, alkylaryl, heteroalkylaryl, alkylheteroaryl, heteroalkylheteroaryl, alkoxy, aryloxy, heteroalkoxy, heteroaryloxy, alkylthio, arylthio, heteroalkylthio, heteroarylthio, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R$_x$, —OCON(R$_x$)$_2$, —N(R$_x$)$_2$, —SF$_5$, —S(O)R$_x$, —S(O)$_2$R$_x$, —NR$_x$(CO)R$_x$, wherein each occurrence of R$_x$ independently includes aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any one of the aliphatic, alicyclic, heteroaliphatic, heterocyclic, alkylaryl, or alkylheteroaryl substituents are substituted or unsubstituted, branched or unbranched, saturated or unsaturated, and wherein any one of the aromatic, heteroaromatic, aryl, heteroaryl, -(alkyl)aryl or -(alkyl)heteroaryl substituents are substituted or unsubstituted;

wherein two adjacent $R^a$ or $R^a$ and $R^b$ can form a 5- to 7-membered carbocyclic ring or a 5- to 7-membered heterocyclic ring in which one or two carbon atoms are replaced by one or two S, O or NR$^c$;

M may be —NHOH.

According to an embodiment, in the compound of the present invention wherein

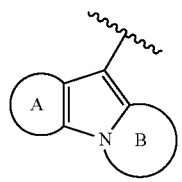

may be selected from the following heterocyclic moieties:

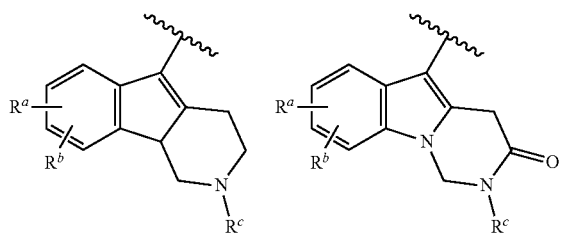

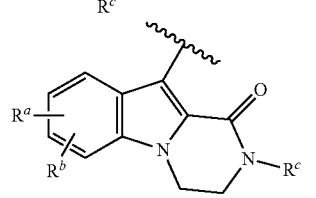

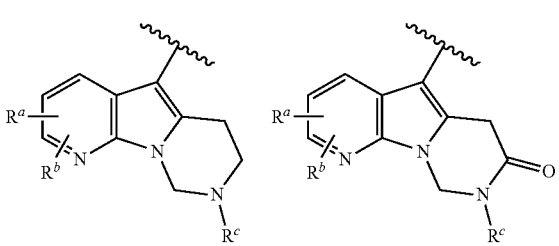

$R^a$, $R^b$ and $R^c$ are defined as above.

According to an embodiment, in the compound of the present invention wherein

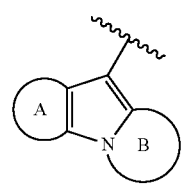

may be selected from the following heterocyclic moieties:

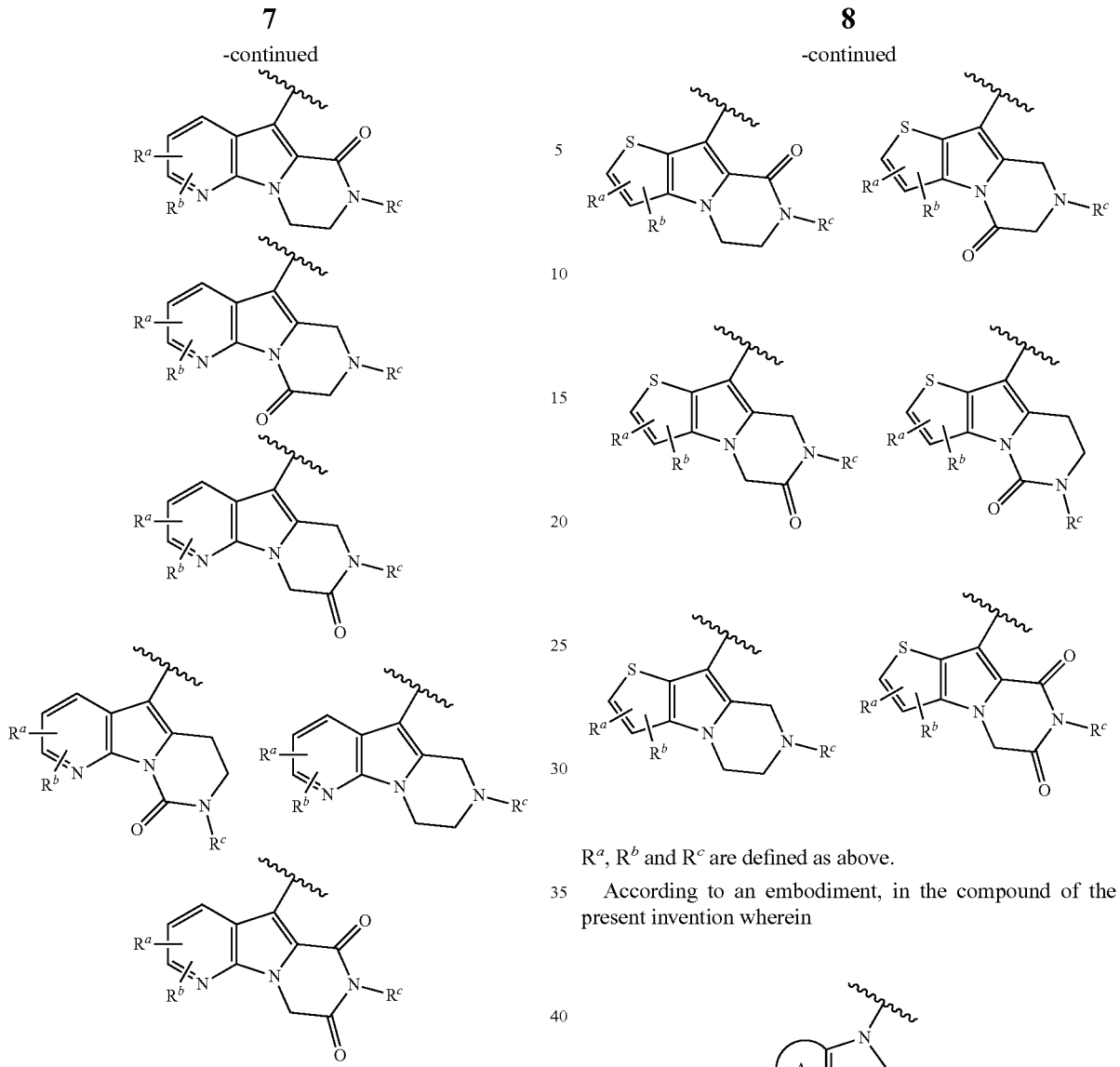
$R^a$, $R^b$ and $R^c$ are defined as above.
According to an embodiment, in the compound of the present invention wherein
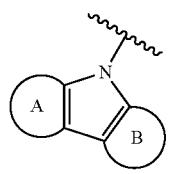
may be selected from the following heterocyclic moieties:
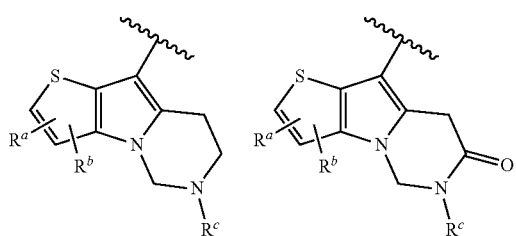
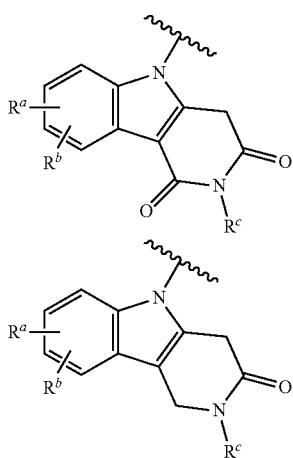

-continued

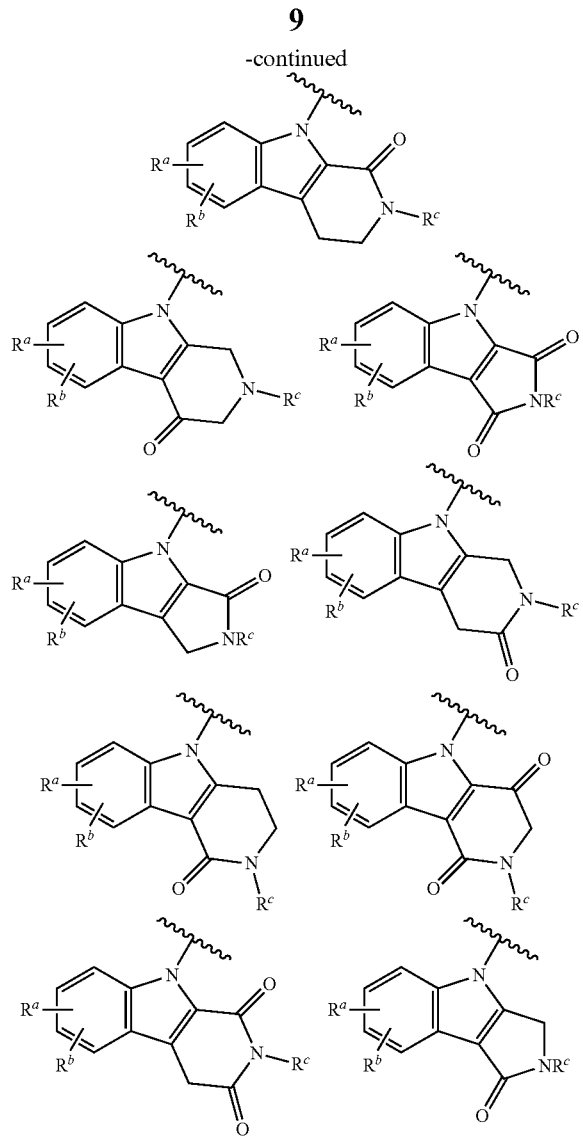

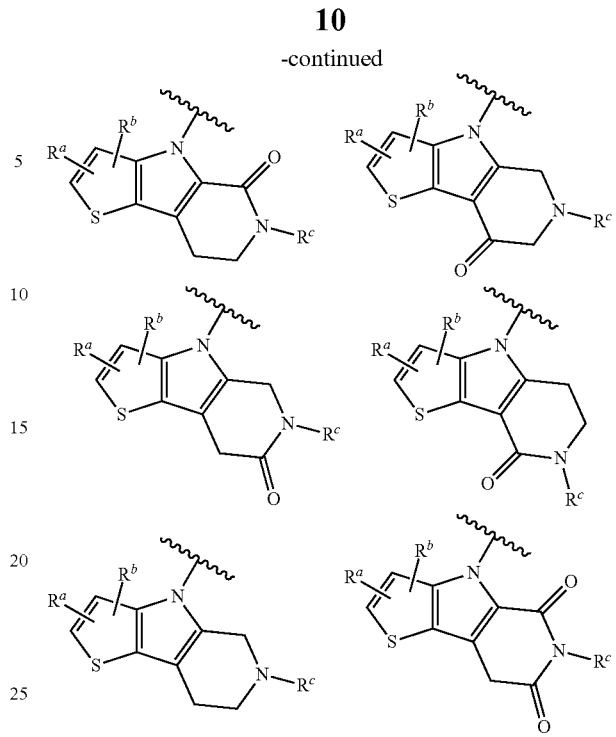

$R^a$, $R^b$ and $R^c$ are defined as above.

According to an embodiment, in the compound of the present invention wherein

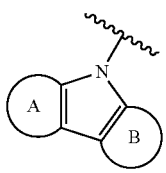

may be selected from the following heterocyclic moieties:

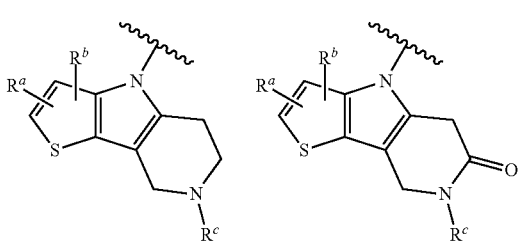

$R^a$, $R^b$ and $R^c$ are defined as above.

According to another embodiment, $R^a$ and $R^b$ may be independently selected from H, $C_1$-$C_6$alkyl, $C_1$-$C_6$cycloalkyl, $CF_3$, $SF_5$, and halo.

According to another embodiment, there is provided a compound of formula I which may be chosen from:

N-hydroxy-4-(2-methyl-1,2,3,4-tetrahydropyrimido[1,6-a]indol-5-ylthio)benzamide,
4-(2,7-dimethyl-1,2,3,4-tetrahydropyrimido[1,6-a]indol-5-ylthio)-N-hydroxybenzamide,
4-(2,8-dimethyl-1,2,3,4-tetrahydropyrimido[1,6-a]indol-5-ylthio)-N-hydroxybenzamide,
4-(8-chloro-2-methyl-1,2,3,4-tetrahydropyrimido[1,6-a]indol-5-ylthio)-N-hydroxybenzamide,
4-(8-fluoro-2-methyl-1,2,3,4-tetrahydropyrimido[1,6-a]indol-5-ylthio)-N-hydroxybenzamide
4-(7-chloro-2-methyl-1,2,3,4-tetrahydropyrimido[1,6-a]indol-5-ylthio)-N-hydroxybenzamide
4-(7-fluoro-2-methyl-1,2,3,4-tetrahydropyrimido[1,6-a]indol-5-ylthio)-N-hydroxybenzamide,
N-hydroxy-4-(2-methyl-7-(trifluoromethyl)-1,2,3,4-tetrahydropyrimido[1,6-a]indol-5-ylthio)benzamide,
N-hydroxy-4-(2-methyl-8-(trifluoromethyl)-1,2,3,4-tetrahydropyrimido[1,6-a]indol-5-ylthio)benzamide,
N-hydroxy-4-[(8-methyl-6,7,8,9-tetrahydropyrido[3',2':4,5]pyrrolo[1,2-c]pyrimidin-5-yl)sulfanyl]benzamide,
N-hydroxy-4-[(7-methyl-6,7,8,9-tetrahydropyrido[3',2':4,5]pyrrolo[1,2-a]pyrazin-5-yl)sulfanyl]benzamide,
N-hydroxy-4-[(7-methyl-6-oxo-6,7,8,9-tetrahydropyrido[3',2':4,5]pyrrolo[1,2-a]pyrazin-5-yl)sulfanyl]benzamide,
N-hydroxy-4-(2-methyl-1,2,3,4-tetrahydropyrazino[1,2-a]indol-10-ylthio)benzamide,
4-(8-chloro-2-methyl-1,2,3,4-tetrahydropyrazino[1,2-a]indol-10-ylthio)-N-hydroxybenzamide,
4-(8-fluoro-2-methyl-1,2,3,4-tetrahydropyrazino[1,2-a]indol-10-ylthio)-N-hydroxybenzamide,
4-(2,8-dimethyl-1,2,3,4-tetrahydropyrazino[1,2-a]indol-10-ylthio)-N-hydroxybenzamide, 4-(6-fluoro-2-methyl-1,2,3,4-tetrahydropyrazino[1,2-a]in-dol-10-ylthio)-N-hydroxybenzamide,
4-(6-chloro-8-fluoro-2-methyl-1,2,3,4-tetrahydropyrazino[1,2-a]indol-10-ylthio)-N-hydroxybenzamide,
4-(6,8-difluoro-2-methyl-1,2,3,4-tetrahydropyrazino[1,2-a]indol-10-ylthio)-N-hydroxybenzamide,
4-(6,8-difluoro-2-methyl-1-oxo-1,2,3,4-tetrahydropyrazino[1,2-a]indol-10-ylthio)-N-hydroxybenzamide,
4-(8-chloro-6-fluoro-2-methyl-1-oxo-1,2,3,4-tetrahydropyrazino[1,2-a]indol-10-ylthio)-N-hydroxybenzamide,
4-(8-chloro-2-methyl-1-oxo-1,2,3,4-tetrahydropyrazino[1,2-a]indol-10-ylthio)-N-hydroxybenzamide,
4-(8-fluoro-2-methyl-1-oxo-1,2,3,4-tetrahydropyrazino[1,2-a]indol-10-ylthio)-N-hydroxybenzamide,
N-hydroxy-4-(2-methyl-1-oxo-1,2,3,4-tetrahydropyrazino[1,2-a]indol-10-ylthio)benzamide,
N-hydroxy-4-((2-methyl-1-oxo-1,2,3,4-tetrahydropyrazino[1,2-a]indol-10-yl)methyl)benzamide,
4-((8-fluoro-2-methyl-1-oxo-1,2,3,4-tetrahydropyrazino[1,2-a]indol-10-yl)methyl)-N-hydroxybenzamide,
4-((6,8-difluoro-2-methyl-1-oxo-1,2,3,4-tetrahydropyrazino[1,2-a]indol-10-yl)methyl)-N-hydroxybenzamide,
4-((6,8-difluoro-2-methyl-1,2,3,4-tetrahydropyrazino[1,2-a]indol-10-yl)methyl)-N-hydroxybenzamide,
N-hydroxy-4-((2-methyl-1,2,3,4-tetrahydropyrazino[1,2-a]indol-10-yl)methyl)benzamide,
N-hydroxy-4-((2-methyl-1,2,3,4-tetrahydropyrimido[1,6-a]indol-5-yl)methyl)benzamide,
4-((7-fluoro-2-methyl-1,2,3,4-tetrahydropyrimido[1,6-a]indol-5-yl)methyl)-N-hydroxybenzamide,
4-((7-chloro-2-methyl-1,2,3,4-tetrahydropyrimido[1,6-a]indol-5-yl)methyl)-N-hydroxybenzamide,
4-((7-chloro-9-fluoro-2-methyl-1,2,3,4-tetrahydropyrimido[1,6-a]indol-5-yl)methyl)-N-hydroxybenzamide,
4-((7,9-difluoro-2-methyl-1,2,3,4-tetrahydropyrimido[1,6-a]indol-5-yl)methyl)-N-hydroxybenzamide,
4-(7,9-difluoro-2-methyl-1,2,3,4-tetrahydropyrimido[1,6-a]indole-5-carbonyl)-N-hydroxybenzamide,
N-hydroxy-4-(2-methyl-1,2,3,4-tetrahydropyrimido[1,6-a]indole-5-carbonyl)benzamide,
N-hydroxy-4-[(7-methyl-6-oxo-6,7,8,9-tetrahydropyrido[3',2':4,5]pyrrolo[1,2-a]pyrazin-5-yl)methyl]benzamide,
N-hydroxy-4-[(7-methyl-6,7,8,9-tetrahydropyrido[3',2':4,5]pyrrolo[1,2-a]pyrazin-5-yl)methyl]benzamide,
N-hydroxy-4-[(8-methyl-6,7,8,9-tetrahydropyrido[3',2':4,5]pyrrolo[1,2-c]pyrimidin-5-yl)methyl]benzamide,
N-hydroxy-4-[(6-methyl-5,6,7,8-tetrahydrothieno[2',3':4,5]pyrrolo[1,2-c]pyrimidin-9-yl)methyl]benzamide,
4-[(2,6-dimethyl-5,6,7,8-tetrahydrothieno[2',3':4,5]pyrrolo[1,2-c]pyrimidin-9-yl)methyl]-N-hydroxybenzamide,
4-[(2,6-dimethyl-5,6,7,8-tetrahydrothieno[2',3':4,5]pyrrolo[1,2-c]pyrimidin-9-yl)sulfanyl]-N-hydroxybenzamide,
4-[(2,7-dimethyl-5,6,7,8-tetrahydrothieno[2',3':4,5]pyrrolo[1,2-a]pyrazin-9-yl)sulfanyl]-N-hydroxybenzamide,
4-[(2,7-dimethyl-8-oxo-5,6,7,8-tetrahydrothieno[2',3':4,5]pyrrolo[1,2-a]pyrazin-9-yl)sulfanyl]-N-hydroxybenzamide,
N-hydroxy-4-[(7-methyl-8-oxo-5,6,7,8-tetrahydrothieno[2',3':4,5]pyrrolo[1,2-a]pyrazin-9-yl)sulfanyl]benzamide,
N-hydroxy-4-[(7-methyl-5,6,7,8-tetrahydrothieno[2',3':4,5]pyrrolo[1,2-a]pyrazin-9-yl)methyl]benzamide,
N-hydroxy-4-[(7-methyl-8-oxo-5,6,7,8-tetrahydrothieno[2',3':4,5]pyrrolo[1,2-a]pyrazin-9-yl)methyl]benzamide,
4-[(2,7-dimethyl-8-oxo-5,6,7,8-tetrahydrothieno[2',3':4,5]pyrrolo[1,2-a]pyrazin-9-yl)methyl]-N-hydroxybenzamide,
4-(2,8-dimethyl-1-oxo-1,2,3,4-tetrahydropyrazino[1,2-a]indol-10-ylthio)-N-hydroxybenzamide,
N-hydroxy-4-[(7-methyl-5,6,7,8-tetrahydro-4H-thieno[2',3':4,5]pyrrolo[3,2-c]pyridin-4-yl)methyl]benzamide,
4-[(2,7-dimethyl-5,6,7,8-tetrahydro-4H-thieno[2',3':4,5]pyrrolo[3,2-c]pyridin-4-yl)methyl]-N-hydroxybenzamide,
4-[(2,7-dimethyl-6-oxo-5,6,7,8-tetrahydro-4H-thieno[2',3':4,5]pyrrolo[3,2-c]pyridin-4-yl)methyl]-N-hydroxybenzamide,
4-[(2,7-dimethyl-8-oxo-5,6,7,8-tetrahydro-4H-thieno[2',3':4,5]pyrrolo[3,2-c]pyridin-4-yl)methyl]-N-hydroxybenzamide,
N-hydroxy-4-[(6-methyl-5-oxo-5,6,7,8-tetrahydro-9H-pyrido[3',4':4,5]pyrrolo[2,3-b]pyridin-9-yl)methyl]benzamide,
N-hydroxy-4-[(6-methyl-5,6,7,8-tetrahydro-9H-pyrido[3',4':4,5]pyrrolo[2,3-b]pyridin-9-yl)methyl]benzamide,
N-hydroxy-4-[(6-methyl-7-oxo-5,6,7,8-tetrahydro-9H-pyrido[3',4':4,5]pyrrolo[2,3-b]pyridin-9-yl)methyl]benzamide,
N-hydroxy-4-[(7-methyl-5,6,7,8-tetrahydro-9H-pyrido[4',3':4,5]pyrrolo[2,3-b]pyridin-9-yl)methyl]benzamide,
N-hydroxy-4-[(7-methyl-6-oxo-5,6,7,8-tetrahydro-9H-pyrido[4',3':4,5]pyrrolo[2,3-b]pyridin-9-yl)methyl]benzamide,
N-hydroxy-4-[(6-methyl-7-oxo-5,6,7,8-tetrahydro-4H-thieno[2',3':4,5]pyrrolo[2,3-c]pyridin-4-yl)methyl]benzamide,
4-[(2,6-dimethyl-7-oxo-5,6,7,8-tetrahydro-4H-thieno[2',3':4,5]pyrrolo[2,3-c]pyridin-4-yl)methyl]-N-hydroxybenzamide,
4-[(2,6-dimethyl-5,6,7,8-tetrahydro-4H-thieno[2',3':4,5]pyrrolo[2,3-c]pyridin-4-yl)methyl]-N-hydroxybenzamide,
4-[(2,6-dimethyl-5-oxo-5,6,7,8-tetrahydro-4H-thieno[2',3':4,5]pyrrolo[2,3-c]pyridin-4-yl)methyl]-N-hydroxybenzamide,
N-hydroxy-4-((2-methyl-3-oxo-3,4-dihydro-1H-pyrido[3,4-b]indol-9(2H)-yl)methyl)benzamide,
N-hydroxy-4-((2-methyl-1-oxo-3,4-dihydro-1H-pyrido[3,4-b]indol-9(2H)-yl)methyl)benzamide,
N-hydroxy-4-((2-methyl-3-oxo-3,4-dihydro-1H-pyrido[4,3-b]indol-5(2H)-yl)methyl)benzamide,
N-hydroxy-4-((2-methyl-1,3-dioxo-3,4-dihydro-1H-pyrido[4,3-b]indol-5(2H)-yl)methyl)benzamide, and
N-hydroxy-4-((2-methyl-1-oxo-3,4-dihydro-1H-pyrido[4,3-b]indol-5(2H)-yl)methyl)benzamide.

According to another embodiment, there is provided a pharmaceutical composition comprising a combination of a compound of the present invention and a second anti-cancer agent selected from a cytotoxic agent, a antimitotic agent, an anti-metabolite, a proteasome inhibitor, a monoclonal antibody, a kinase inhibitor and a pharmaceutically acceptable carrier.

According to another embodiment, there is provided a pharmaceutical composition comprising a compound of the present invention and a pharmaceutically acceptable carrier.

According to another embodiment, there is provided a method of treating a disease or condition comprising administering a therapeutically effective amount of a compound of the present invention to an individual in need thereof.

According to another embodiment, there is provided a method of treating a disease or condition comprising administering a therapeutically effective amount of a compound of the present invention together with radiation to an individual in need thereof.

The disease or condition may be a cancer, a neurological disease, a neurodegenerative disorder, a stroke, a traumatic brain injury, parasitic infection, inflammation or an autoimmune disease.

According to another embodiment, there is provided a use of a compound of the present invention, or the composition of any one of the present invention for the treatment of a disease or condition.

According to another embodiment, there is provided a use of a compound of the present invention, or the composition of the present invention for the fabrication of a medicament for the treatment of a disease or condition.

The disease or condition may be a cancer, a neurological disease, a neurodegenerative disorder, a stroke, a traumatic brain injury, an inflammation, an autoimmune disease or a parasitic infection.

The following terms are defined below.

The term "alkyl" as employed herein refers to straight and branched chain aliphatic groups having from 1 to 12 carbon atoms, preferably 1-8 carbon atoms, and more preferably 1-6 carbon atoms, which may be optionally substituted with one, two or three substituents. Unless otherwise explicitly stated, the term "alkyl" is meant to include saturated, unsaturated, and partially unsaturated aliphatic groups. When unsaturated groups are particularly intended, the terms "alkenyl" or "alkynyl" will be used. When only saturated groups are intended, the term "saturated alkyl" will be used. Preferred saturated alkyl groups include, without limitation, methyl, ethyl, propyl, isopropyl, butyl, isobutyl, sec-butyl, tert-butyl, pentyl, and hexyl.

An "alkylene" group is an alkyl group, as defined hereinabove, that is positioned between and serves to connect two other chemical groups. The term "alkylene" includes saturated, unsaturated and partially unsaturated alkyl groups. Where the term "alkylene" includes a descriptor indicating the number of carbon atoms or a range in the number of carbon atoms, e.g., C1-8 alkylene, the number of carbon atoms refers to the length of the linear chain connecting the two chemical groups between which the alkylene group is positioned. Any of the carbon atoms of the alkylene group may be optionally substituted, as described below, and the substituents may contain additional carbon atoms, as exemplified, but not limited, by —$CH_2CH_2CH_2CH_2$—, —$CH_2CH=CHCH_2$—, —$CH_2C\equiv CCH_2$—, —$CH_2CH_2CH(CH_2CH_2CH_3)CH_2$—.

The term "cycloalkyl" or "carbocycle" as employed herein includes saturated and partially unsaturated cyclic hydrocarbon groups having from 3 to about 12 carbons, preferably from 3 to about 8 carbons, and more preferably from 3 to about carbons, wherein the cycloalkyl group additionally may be optionally substituted 5 Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is an aromatic moiety comprising one to three aromatic rings, which may be optionally substituted. Preferably, the aryl group is a $C_6$-$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$-$C_6$)alkaryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methyl naphthyl.

A "heterocyclic moiety" or "heterocyclyl" is a ring structure having from about 3 to about 8 atoms, wherein one or more atoms are selected from the group consisting of N, O, and S. In some embodiments, the heterocyclic group is saturated or partially saturated. In these embodiments, the heterocyclic group may be optionally substituted on carbon at one or more positions, and may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred saturated heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl or heteroaryl group. Examples of such fused heterocyles include, without limitation, tetrahydroquinoline and dihydrobenzofuran.

In some other embodiments, the heterocyclic moiety is a heteroaryl group. As used herein, the term "heteroaryl" refers to groups having 5 to 14 ring atoms, preferably 5, 6, 9, or 10 ring atoms; having 6, 10, or 14 it electrons shared in a cyclic array; and having, in addition to carbon atoms, from one to about three heteroatoms selected from the group consisting of N, O, and S. Preferred heteroaryl groups include, without limitation, thienyl, benzothienyl, filranyl, benzofuranyl, dibenzofuranyl, pyrrolyl, imidazolyl, pyrazolyl, pyridyl, pyrazinyl, pyrimidinyl, indolyl, quinolinyl, isoquinolinyl, quinoxalinyl, tetrazolyl, oxazolyl, thiazolyl, and isoxazolyl.

As employed herein, a "substituted" alkyl, cycloalkyl, aryl, heteroaryl, or heterocyclic group is one having from one to about four, preferably from one to about three, more preferably one or two, non-hydrogen substituents. Suitable substituents include, without limitation, halo, hydroxy, oxo, oxin-dno, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, areniesulfonyl, alkanesulfonamido, arenesulfonamido, aralkylsulfonamido, acyl, acyloxy, cyano, and ureido groups.

The term "halogen" or "halo" as employed herein refers to chlorine, bromine, fluorine, or iodine.

The term "prodrug" refers to compounds which are drug precursors which, following administration to a subject and subsequent absorption, is converted to an active species in vivo via some process, such as a metabolic process. Other products from the conversion process are easily disposed of by the body. More preferred prodrugs produce products from the conversion process which are generally accepted as safe.

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

DETAILED DESCRIPTION

The present invention provides novel HDAC6 inhibitors and methods of preparing and potential therapeutic uses of these novel compounds. The inventive compound may be useful in the treatment of proliferative diseases such as cancer and neurologic disorders.

The present invention provides in part compounds of Formula I, which are useful as HDAC6 inhibitors:

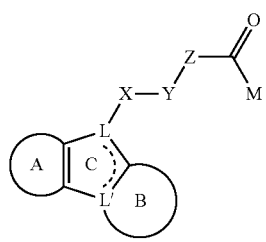

Formula I or a pharmaceutically acceptable salt thereof, wherein:

L and L' are selected from a nitrogen atom or carbon atom with the proviso that L and L' are not the same at the same time;

X is O, S, $CH_2$, C(O), or a bond with the proviso that X is not O and S when L is a nitrogen atom;

Y is a bond, an aryl, or a heteroaryl which is optionally substituted;

Z is a bond or selected from the groups consisting of $C_{1-8}$alkylene, $NR^a$, $C(O)C_{1-8}$alkylene, $C_{1-8}$alkyleneNR$^a$, $C_{1-6}$alkylenearyleneC$_{1-6}$alkylene, $C_{2-8}$alkenylene, $C_{1-6}$alkylenearylene, $C_{1-6}$alkyleneheteroarylene, $C_{2-6}$alkenylenearyleneC$_{1-6}$alkylene; all of these groups are optionally substituted with one or more $R^a$;

M is selected from —NHOH, $CH_2$SH, $CH_2$SC(O)$C_{1-8}$alkyl, $CH_2$SC(O)aryl, $CH_2$SC(O)heteroaryl, $CH2_SC(O)C_{1-8}$alkylenearyl, $CH_2$SC(O)$C_{1-8}$alkylenheteroaryl or

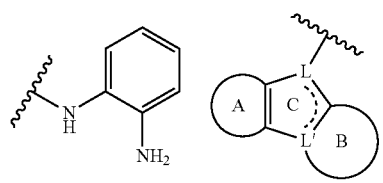

is selected from the following heterocyclic moieties:

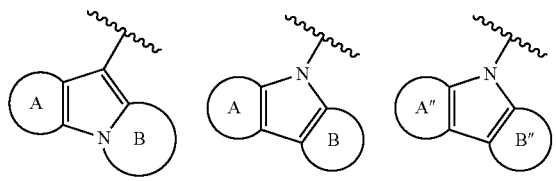

wherein

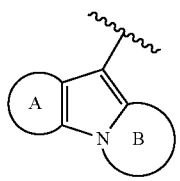

is selected from the following heterocyclic moieties:

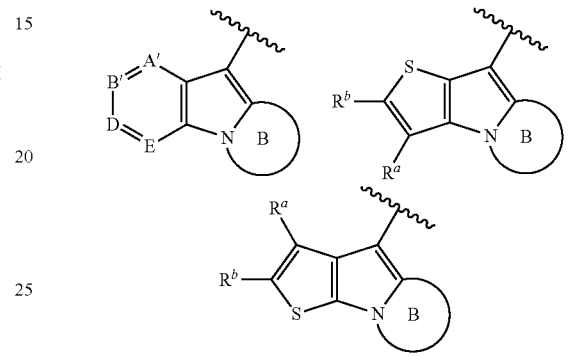

wherein each of A', B', D and E is independently selected from N, and C(R$^a$);

$R^a$ and $R^b$ are independently selected from, but not limited to: hydrogen, aliphatic, alicyclic, heteroaliphatic, heterocyclic, aromatic, heteroaromatic, aryl, heteroaryl, alkylaryl, heteroalkylaryl, alkylheteroaryl, heteroalkylheteroaryl, alkoxy, aryloxy, heteroalkoxy, heteroaryloxy, alkylthio, arylthio, heteroalkylthio, heteroarylthio, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO2(R$_x$), —CON(R$_x$)$_2$, —OC(O)R$_x$, —OCO$_2$R$_x$, —OCON(R$_x$)$_2$, —N(R$_x$)$_2$, —SF$_5$, —S(O)R$_x$, —S(O)$_2$R$_x$, —NR$_x$(CO)R$_x$ wherein each occurrence of R$_x$ independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Preferably, R$^a$ and R$^b$ are independently selected from H, $C_1$-$C_6$alkyl, $C_1$-$C_6$cycloalkyl, CF$_3$, SF$_5$, halo. Two adjacent R$^a$ or R$^a$ and R$^b$ can form a 5- to 7-membered carbocyclic ring or a 5- to 7-membered heterocyclic ring in which one or two carbon atoms can be optionally replaced by one or two S, O or NR$^c$;

wherein, in

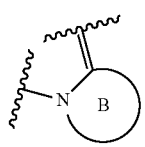

B ring is a 5 to 7 membered carbocyclic ring in which one or more of the carbon atoms is optionally replaced with C(O), O, S, NR$^c$ wherein R$^c$ is selected from hydrogen, C1-C6alkyl, C1-C6cycloalkyl, aryl, heteroaryl, C1-C$_6$alkylenearyl, C$_1$-C$_6$alkyleneheteroaryl, SO$_2$R$^e$, C(O)R$^e$. R$^e$ is C$_1$-C$_6$alkyl, C$_1$-C$_6$cycloalkyl, aryl, heterocycle, heteroaryl, C$_1$-C$_6$alkylenearyl, C$_1$-C$_6$alkyleneheteroaryl, with the proviso that there are no N—O or N—S bond in the molecules.

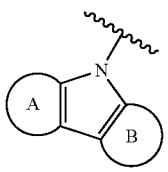

is selected from the following heterocyclic moieties:

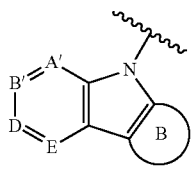 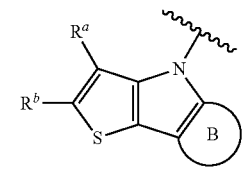

wherein each of A', B', D and E is independently selected from N, and C(R$^a$) with the proviso that at least one of A', B', C and D is N, and X in Formula I is not S, or O;

R$^a$ and R$^b$ are independently selected from, but not limited to: hydrogen, aliphatic, alicyclic, heteroaliphatic, heterocyclic, aromatic, heteroaromatic, aryl, heteroaryl, alkylaryl, heteroalkylaryl, alkylheteroaryl, heteroalkylheteroaryl, alkoxy, aryloxy, heteroalkoxy, heteroaryloxy, alkylthio, arylthio, heteroalkylthio, heteroarylthio, F, Cl, Br, I, —OH, —NO$_2$, —CN, —CF$_3$, —CH$_2$CF$_3$, —CHCl$_2$, —CH$_2$OH, —CH$_2$CH$_2$OH, —CH$_2$NH$_2$, —CH$_2$SO$_2$CH$_3$, —C(O)R$_x$, —CO$_2$(R$_x$), —CON(R$_x$)$_2$, —OC(O)R$_x$, —OCO$_2$R, —OCON(R$_x$)$_2$, —N(R$_x$)$_2$, —SF$_5$, —S(O)R$_x$, —S(O)$_2$R$_x$, —NR$_x$(CO)R$_x$ wherein each occurrence of Rx independently includes, but is not limited to, aliphatic, alicyclic, heteroaliphatic, heterocyclic, aromatic, heteroaromatic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aromatic, heteroaromatic, aryl, heteroaryl, -(alkyl)aryl or -(alkyl)heteroaryl substituents described above and herein may be substituted or unsubstituted. Preferably, R$^a$ and R$^b$ are independently selected from H, C$_1$-C$_6$alkyl, C$_1$-C$_6$cycloalkyl, CF$_3$, SF$_5$, halo. Two adjacent R$^a$ or R$^a$ and R$^b$ can form a 5- to 7-membered carbocyclic ring or a 5- to 7-membered heterocyclic ring in which one or two carbon atoms can be optionally replaced by one or two S, O or NR$^c$;

wherein, in

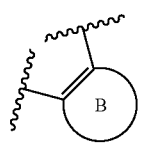

B ring is a 5 to 7 membered carbocyclic ring in which one or more of the carbon atoms is optionally replaced with C(O), O, S, NR$^c$ wherein R$^c$ is selected from hydrogen, C$_1$-C$_6$alkyl, C$_1$-C$_6$cycloalkyl, aryl, heterocycle, heteroaryl, C$_1$-C$_6$alkylenearyl, C$_1$-C$_6$alkyleneheteroaryl, SO$_2$Re, C(O)R$^e$. R$^e$ is C$_1$-C$_6$alkyl, C$_1$-C$_6$cycloalkyl, aryl, heterocycle, heteroaryl, C$_1$-C$_6$alkylenearyl, C$_1$-C$_6$alkyleneheteroaryl, with the proviso that there are no N—O or N—S bond in the molecules.

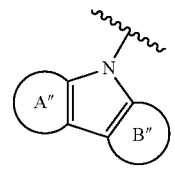

is selected from the following heterocyclic moieties:

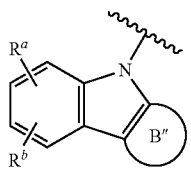

wherein, in

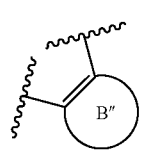

B ring is selected from the following:

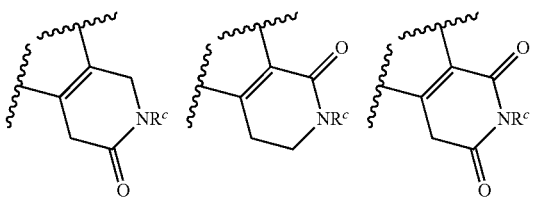

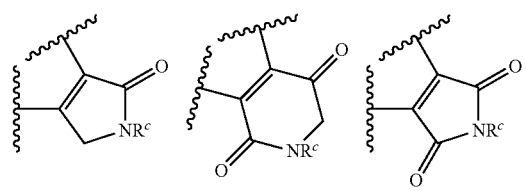

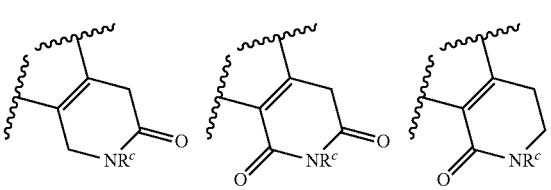

-continued
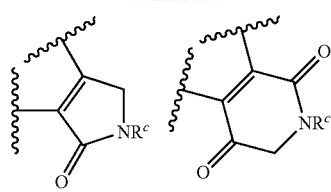
which are optionally substituted with one or more $R^a$ and $R^b$.
In one embodiment,
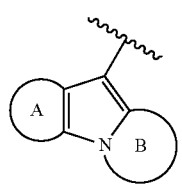
is selected from the following heterocyclic moieties:
-continued
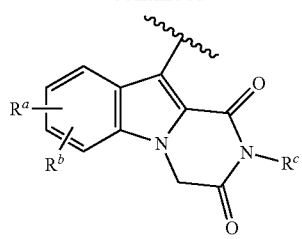
In another embodiment,
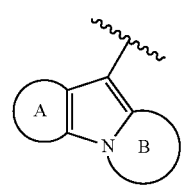
is selected from the following heterocyclic moieties:
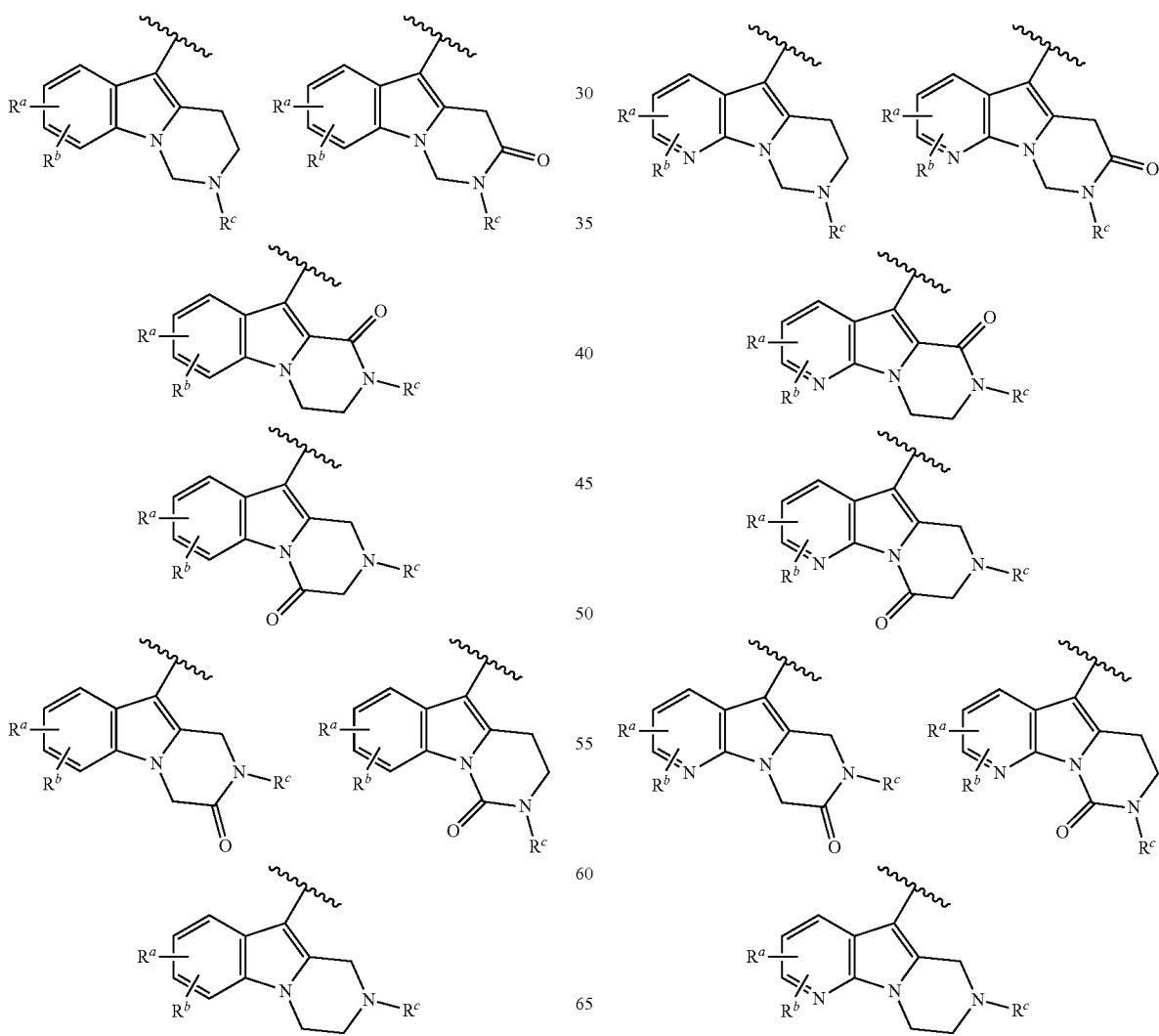

-continued

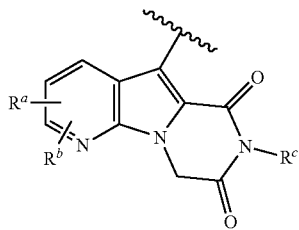

In another embodiment,

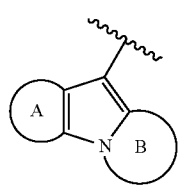

is selected from the following heterocyclic moieties:

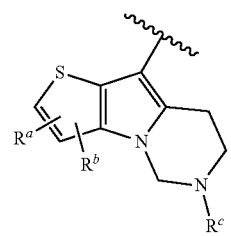   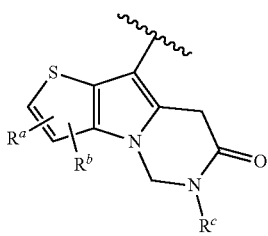

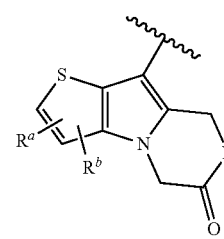   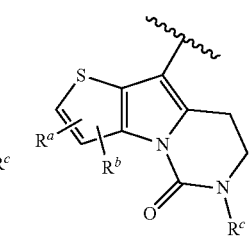

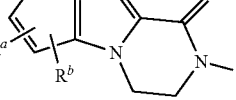   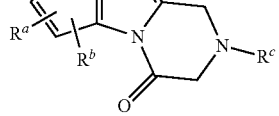

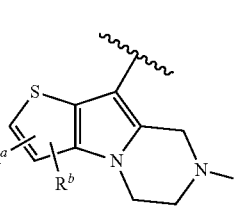   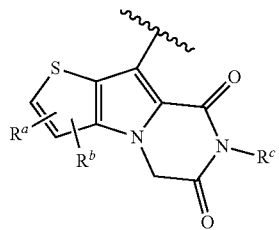

In another embodiment,

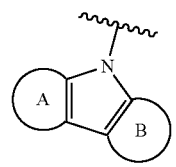

is selected from the following heterocyclic moieties:

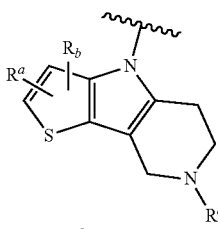   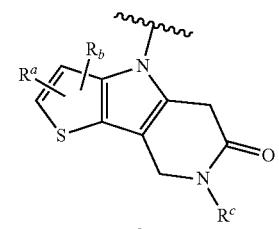

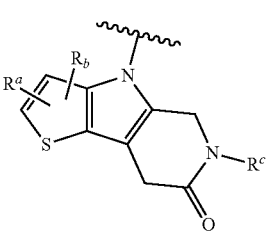   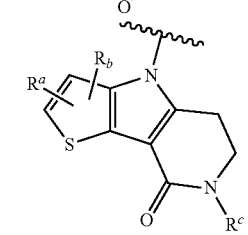

More specifically, the invention relates to compounds of Formula I which are:
N-hydroxy-4-(2-methyl-1,2,3,4-tetrahydropyrimido[1,6-a]indol-5-ylthio)benzamide,
4-(2,7-dimethyl-1,2,3,4-tetrahydropyrimido[1,6-a]indol-5-ylthio)-N-hydroxybenzamide,
4-(2,8-dimethyl-1,2,3,4-tetrahydropyrimido[1,6-a]indol-5-ylthio)-N-hydroxybenzamide,
4-(8-chloro-2-methyl-1,2,3,4-tetrahydropyrimido[1,6-a]indol-5-ylthio)-N-hydroxybenzamide,
4-(8-fluoro-2-methyl-1,2,3,4-tetrahydropyrimido[1,6-a]indol-5-ylthio)-N-hydroxybenzamide
4-(7-chloro-2-methyl-1,2,3,4-tetrahydropyrimido[1,6-a]indol-5-ylthio)-N-hydroxybenzamide
4-(7-fluoro-2-methyl-1,2,3,4-tetrahydropyrimido[1,6-a]indol-5-ylthio)-N-hydroxybenzamide,
N-hydroxy-4-(2-methyl-7-(trifluoromethyl)-1,2,3,4-tetrahydropyrimido[1,6-a]indol-5-ylthio)benzamide,
N-hydroxy-4-(2-methyl-8-(trifluoromethyl)-1,2,3,4-tetrahydropyrimido[1,6-a]indol-5-ylthio)benzamide, N-hydroxy-4-[(8-methyl-6,7,8,9-tetrahydropyrido[3,2':4,5]pyrrolo[1,2-c]pyrimidin-5-yl)sulfanyl]benzamide,
N-hydroxy-4-[(7-methyl-6,7,8,9-tetrahydropyrido[3',2':4,5]pyrrolo[1,2-a]pyrazin-5-yl)sulfanyl]benzamide,
N-hydroxy-4-[(7-methyl-6-oxo-6,7,8,9-tetrahydropyrido[3',2':4,5]pyrrolo[1,2-a]pyrazin-5-yl)sulfanyl]benzamide,
N-hydroxy-4-(2-methyl-1,2,3,4-tetrahydropyrazino[1,2-a]indol-10-ylthio)benzamide,
4-(8-chloro-2-methyl-1,2,3,4-tetrahydropyrazino[1,2-a]indol-10-ylthio)-N-hydroxybenzamide,
4-(8-fluoro-2-methyl-1,2,3,4-tetrahydropyrazino[1,2-a]indol-10-ylthio)-N-hydroxybenzamide,
4-(2,8-dimethyl-1,2,3,4-tetrahydropyrazino[1,2-a]indol-10-ylthio)-N-hydroxybenzamide,
4-(6-fluoro-2-methyl-1,2,3,4-tetrahydropyrazino[1,2-a]indol-10-ylthio)-N-hydroxybenzamide,
4-(6-chloro-8-fluoro-2-methyl-1,2,3,4-tetrahydropyrazino[1,2-a]indol-10-ylthio)-N-hydroxybenzamide,
4-(6,8-difluoro-2-methyl-1,2,3,4-tetrahydropyrazino[1,2-a]indol-10-ylthio)-N-hydroxybenzamide,
4-(6,8-difluoro-2-methyl-1-oxo-1,2,3,4-tetrahydropyrazino[1,2-a]indol-10-ylthio)-N-hydroxybenzamide,
4-(8-chloro-6-fluoro-2-methyl-1-oxo-1,2,3,4-tetrahydropyrazino[1,2-a]indol-10-ylthio)-N-hydroxybenzamide,
4-(8-chloro-2-methyl-1-oxo-1,2,3,4-tetrahydropyrazino[1,2-a]indol-10-ylthio)-N-hydroxybenzamide,
4-(8-fluoro-2-methyl-1-oxo-1,2,3,4-tetrahydropyrazino[1,2-a]indol-10-ylthio)-N-hydroxybenzamide,
N-hydroxy-4-(2-methyl-1-oxo-1,2,3,4-tetrahydropyrazino[1,2-a]indol-10-ylthio)benzamide,
N-hydroxy-4-((2-methyl-1-oxo-1,2,3,4-tetrahydropyrazino[1,2-a]indol-10-yl)methyl)benzamide,
4-((8-fluoro-2-methyl-1-oxo-1,2,3,4-tetrahydropyrazino[1,2-a]indol-10-yl)methyl)-N-hydroxybenzamide,
4-((6,8-difluoro-2-methyl-1-oxo-1,2,3,4-tetrahydropyrazino[1,2-a]indol-10-yl)methyl)-N-hydroxybenzamide,
4-((6,8-difluoro-2-methyl-1,2,3,4-tetrahydropyrazino[1,2-a]indol-10-yl)methyl)-N-hydroxybenzamide,
N-hydroxy-4-((2-methyl-1,2,3,4-tetrahydropyrazino[1,2-a]indol-10-yl)methyl)benzamide,
N-hydroxy-4-((2-methyl-1,2,3,4-tetrahydropyrimido[1,6-a]indol-5-yl)methyl)benzamide,
4-((7-fluoro-2-methyl-1,2,3,4-tetrahydropyrimido[1,6-a]indol-5-yl)methyl)-N-hydroxybenzamide,
4-((7-chloro-2-methyl-1,2,3,4-tetrahydropyrimido[1,6-a]indol-5-yl)methyl)-N-hydroxybenzamide,
4-((7-chloro-9-fluoro-2-methyl-1,2,3,4-tetrahydropyrimido[1,6-a]indol-5-yl)methyl)-N-hydroxybenzamide,
4-((7,9-difluoro-2-methyl-1,2,3,4-tetrahydropyrimido[1,6-a]indol-5-yl)methyl)-N-hydroxybenzamide,
4-(7,9-difluoro-2-methyl-1,2,3,4-tetrahydropyrimido[1,6-a]indole-5-carbonyl)-N-hydroxybenzamide,
N-hydroxy-4-(2-methyl-1,2,3,4-tetrahydropyrimido[1,6-a]indole-5-carbonyl)benzamide,
N-hydroxy-4-[(7-methyl-6-oxo-6,7,8,9-tetrahydropyrido[3',2':4,5]pyrrolo[1,2-a]pyrazin-5-yl)methyl]benzamide,
N-hydroxy-4-[(7-methyl-6,7,8,9-tetrahydropyrido[3',2':4,5]pyrrolo[1,2-a]pyrazin-5-yl)methyl]benzamide,
N-hydroxy-4-[(8-methyl-6,7,8,9-tetrahydropyrido[3',2':4,5]pyrrolo[1,2-c]pyrimidin-5-yl)methyl]benzamide,
N-hydroxy-4-[(6-methyl-5,6,7,8-tetrahydrothieno[2',3':4,5]pyrrolo[1,2-c]pyrimidin-9-yl)methyl]benzamide,
4-[(2,6-dimethyl-5,6,7,8-tetrahydrothieno[2',3':4,5]pyrrolo[1,2-c]pyrimidin-9-yl)methyl]-N-hydroxybenzamide,
4-[(2,6-dimethyl-5,6,7,8-tetrahydrothieno[2',3':4,5]pyrrolo[1,2-c]pyrimidin-9-yl)sulfanyl]-N-hydroxybenzamide,
4-[(2,7-dimethyl-5,6,7,8-tetrahydrothieno[2',3':4,5]pyrrolo[1,2-a]pyrazin-9-yl)sulfanyl]-N-hydroxybenzamide,
4-[(2,7-dimethyl-8-oxo-5,6,7,8-tetrahydrothieno[2',3':4,5]pyrrolo[1,2-a]pyrazin-9-yl)sulfanyl]-N-hydroxybenzamide,
N-hydroxy-4-[(7-methyl-8-oxo-5,6,7,8-tetrahydrothieno[2',3':4,5]pyrrolo[1,2-a]pyrazin-9-yl)sulfanyl]benzamide,
N-hydroxy-4-[(7-methyl-5,6,7,8-tetrahydrothieno[2',3':4,5]pyrrolo[1,2-a]pyrazin-9-yl)methyl]benzamide,
N-hydroxy-4-[(7-methyl-8-oxo-5,6,7,8-tetrahydrothieno[2',3':4,5]pyrrolo[1,2-a]pyrazin-9-yl)methyl]benzamide,
4-[(2,7-dimethyl-8-oxo-5,6,7,8-tetrahydrothieno[2',3':4,5]pyrrolo[1,2-a]pyrazin-9-yl)methyl]-N-hydroxybenzamide,
4-(2,8-dimethyl-1-oxo-1,2,3,4-tetrahydropyrazino[1,2-a]indol-10-ylthio)-N-hydroxybenzamide,
N-hydroxy-4-[(7-methyl-5,6,7,8-tetrahydro-4H-thieno[2',3':4,5]pyrrolo[3,2-c]pyridin-4-yl)methyl]benzamide,
4-[(2,7-dimethyl-5,6,7,8-tetrahydro-4H-thieno[2',3':4,5]pyrrolo[3,2-c]pyridin-4-yl)methyl]-N-hydroxybenzamide,
4-[(2,7-dimethyl-6-oxo-5,6,7,8-tetrahydro-4H-thieno[2',3':4,5]pyrrolo[3,2-c]pyridin-4-yl)methyl]-N-hydroxybenzamide,
4-[(2,7-dimethyl-8-oxo-5,6,7,8-tetrahydro-4H-thieno[2',3':4,5]pyrrolo[3,2-c]pyridin-4-yl)methyl]-N-hydroxybenzamide,
N-hydroxy-4-[(6-methyl-5-oxo-5,6,7,8-tetrahydro-9H-pyrido[3',4':4,5]pyrrolo[2,3-b]pyridin-9-yl)methyl]benzamide,
N-hydroxy-4-[(6-methyl-5,6,7,8-tetrahydro-9H-pyrido[3',4':4,5]pyrrolo[2,3-b]pyridin-9-yl)methyl]benzamide,
N-hydroxy-4-[(6-methyl-7-oxo-5,6,7,8-tetrahydro-9H-pyrido[3',4':4,5]pyrrolo[2,3-b]pyridin-9-yl)methyl]benzamide,
N-hydroxy-4-[(7-methyl-5,6,7,8-tetrahydro-9H-pyrido[4',3':4,5]pyrrolo[2,3-b]pyridin-9-yl)methyl]benzamide,
N-hydroxy-4-[(7-methyl-6-oxo-5,6,7,8-tetrahydro-9H-pyrido[4',3':4,5]pyrrolo[2,3-b]pyridin-9-yl)methyl]benzamide,
N-hydroxy-4-[(6-methyl-7-oxo-5,6,7,8-tetrahydro-4H-thieno[2',3':4,5]pyrrolo[2,3-c]pyridin-4-yl)methyl]benzamide,
4-[(2,6-dimethyl-7-oxo-5,6,7,8-tetrahydro-4H-thieno[2',3':4,5]pyrrolo[2,3-c]pyridin-4-yl)methyl]-N-hydroxybenzamide,
4-[(2,6-dimethyl-5,6,7,8-tetrahydro-4H-thieno[2',3':4,5]pyrrolo[2,3-c]pyridin-4-yl)methyl]-N-hydroxybenzamide,
4-[(2,6-dimethyl-5-oxo-5,6,7,8-tetrahydro-4H-thieno[2',3':4,5]pyrrolo[2,3-c]pyridin-4-yl)methyl]-N-hydroxybenzamide,
N-hydroxy-4-((2-methyl-3-oxo-3,4-dihydro-1H-pyrido[3,4-b]indol-9(2H)-yl)methyl)benzamide,
N-hydroxy-4-((2-methyl-1-oxo-3,4-dihydro-1H-pyrido[3,4-b]indol-9(2H)-yl)methyl)benzamide,
N-hydroxy-4-((2-methyl-3-oxo-3,4-dihydro-1H-pyrido[4,3-b]indol-5(2H)-yl)methyl)benzamide,
N-hydroxy-4-((2-methyl-1,3-dioxo-3,4-dihydro-1H-pyrido[4,3-b]indol-5(2H)-yl)methyl)benzamide,
N-hydroxy-4-((2-methyl-1-oxo-3,4-dihydro-1H-pyrido[4,3-b]indol-5(2H)-yl)methyl)benzamide, The invention also provides various pharmaceutically acceptable forms of the inventive compounds, for examples, stereoisomers, enantiomers, tautomers, salts, solvates, hydrates, co-crystals, and polymorphs.

One or more than one of the protons in compounds of Formula I can be replaced with deuterium atom(s), thus providing deuterated analogs that may have improved pharmacological activities.

In another aspect, the present invention provides pharmaceutical compositions comprising a therapeutically effective amount of a compound of Formula I and a pharmaceutically acceptable excipient. In certain embodiments, the pharmaceutical composition is useful in the treatment of a proliferative disease such as cancer. Exemplary cancer include, but are not limited to, breast cancer, cervical cancer, colon and rectal cancer, leukemia, lung cancer, melanoma, multiple myeloma, non-Hodgkin's lymphoma, lymphoma, ovarian cancer, pancreatic cancer, prostate cancer, skin cancer, and gastric cancer. In certain embodiments, the inventive compounds are active against leukemia cells and melanoma cells, and thus are useful for the treatment of leukemia (e.g., myeloid, lymphocytic, myelocytic and lymphoblastic leukemia) and malignant melanomas. In certain embodiments, the inventive compounds are useful in the treatment of cutaneous T-cell lymphoma (CTCL). In certain embodiments, the inventive compound specifically inhibits HDAC6. In certain embodiments, the method is used to specifically inhibit tubulin deacetylase activity in a subject or a biological sample. Moreover, the present invention relates also to the combination of a compound of formula I with one or more anticancer agents selected from cytotoxic agents, mitotic poisons, anti-metabolites, proteasome inhibitors and kinase inhibitors, and to the use of that type of combination in the manufacture of medicaments for use in the treatment of cancer.

The compounds of the invention may also be used in combination with radiotherapy in the treatment of cancer.

Compounds of Formula I are also expected to be useful as chemotherapeutic agents in combination with therapeutic agents that include, but are not limited to, angiogenesis inhibitors, antiproliferative agents, kinase inhibitors, receptor tyrosine kinase inhibitors, aurora kinase inhibitors, polo-like kinase inhibitors, bcr-abl kinase inhibitors, growth factor inhibitors, Bcl inhibitors, Mcl inhibitors, COX-2 inhibitors, non-steroidal anti-inflammatory drugs (NSAIDS), antimitotic agents, alkylating agents, antimetabolites, intercalating antibiotics, platinum containing agents, growth factor inhibitors, ionizing radiation, cell cycle inhibitors, enzymes, topoisomerase inhibitors, biologic response modifiers, immunologicals, antibodies, hormonal therapies, retinoidsdeltoids plant alkaloids, proteasome inhibitors, HSP-90 inhibitors, other histone deacetylase inhibitors (HDAC) inhibitors, purine analogs, pyrimidine analogs, MEK inhibitors, CDK inhibitors, ErbB2 receptor inhibitors, mTOR inhibitors and combinations thereof as well as other antitumor agents.

Angiogenesis inhibitors include, but are not limited to, EGFR inhibitors, PDGFR inhibitors, VEGFR inhibitors, TTE2 inhibitors, IGFIR inhibitors, matrix metalloproteinase 2 (MMP-2) inhibitors, matrix metalloproteinase 9 (MMP-9) inhibitors, thrombospondin analogs such as thrombospondin-1 and N—Ac-Sar-Gly-Val-D-allolle-Thr-Nva-He-Arg-Pro-NHCH$_2$CH$_3$ or a salt thereof and analogues of N—Ac-Sar-Gly-Val-D-allolle-Thr-Nva-Ile-Arg-PrO—NHCH$_2$CH$_3$ such as N—Ac-GlyVal-D-alle-Ser-Gln-Ile-Arg-ProNHCH2CH3 or a salt thereof.

Examples of EGFR inhibitors include, but are not limited to, Iressa (gefitinib),
Tarceva (erlotinib or OSI-774), Icotinib, Erbitux (cetuximab), EMD-7200, ABX-EGF, HR3, IgA antibodies, TP-38 (IVAX), EGFR fusion protein, EGF-vaccine, anti-EGFr immunoliposomes and Tykerb (lapatinib).

Examples of PDGFR inhibitors include, but are not limited to, CP-673,451 and CP-868596.

Examples of VEGFR inhibitors include, but are not limited to, Avastin (bevacizumab), Sutent (sunitinib, SUI 1248), Nexavar (sorafenib, BAY43-9006), CP-547,632, axitinib (AG13736), Apatinib, cabozantinib, Zactima (vandetanib, ZD-6474), AEE788, AZD-2171, VEGF trap, Vatalanib (PTK-787, ZK-222584), Macugen, M862, Pazopanib (GW786034), ABT-869 and angiozyme.

Examples of thrombospondin analogs include, but are not limited to, TSP-I and ABT-510.

Examples of aurora kinase inhibitors include, but are not limited to, VX-680, AZD-1152 and MLN-8054. Example of polo-like kinase inhibitors include, but are not limited to, BI-2536.

Examples of bcr-abl kinase inhibitors include, but are not limited to, Gleevec (imatinib), Ponatinib, Nilotinib and Dasatinib (BMS354825).

Examples of platinum containing agents includes, but are not limited to, cisplatin, Paraplatin (carboplatin), eptaplatin, lobaplatin, nedaplatin, Eloxatin (oxaliplatin) or satraplatin.

Examples of mTOR inhibitors includes, but are not limited to, CCI-779, rapamycin, temsirolimus, everolimus, RAD001, INK-128 and ridaforolimus.

Examples of HSP-90 inhibitors includes, but are not limited to, geldanamycin, radicicol, 17-AAG, KOS-953, 17-DMAG, CNF-101, CNF-1010, 17-AAG-nab, NCS-683664, Mycograb, CNF-2024, PU3, PU24FC1, VER49009, IPI-504, SNX-2112 and STA-9090.

Examples of histone deacetylase inhibitors (HDAC) includes, but are not limited to, Suberoylanilide hydroxamic acid (SAHA), MS-275, valproic acid, TSA, LAQ-824, Trapoxin, tubacin, tubastatin, ACY-1215 and Depsipeptide.

Examples of MEK inhibitors include, but are not limited to, PD325901, ARRY-142886, ARRY-438162 and PD98059.

Examples of CDK inhibitors include, but are not limited to, flavopyridol, MCS-5A, CVT-2584, seliciclib (CYC-202, R-roscovitine), ZK-304709, PHA-690509, BMI-1040, GPC-286199, BMS-387,032, PD0332991 and AZD-5438.

Examples of Bcl inhibitors include, but not limited to, Navitoclax, obatoclax.

Examples of COX-2 inhibitors include, but are not limited to, CELEBREX™ (celecoxib), parecoxib, deracoxib, ABT-963, MK-663 (etoricoxib), COX-189 Lumiracoxib), BMS347070, RS 57067, NS-398, Bextra (valdecoxib), paracoxib, Vioxx (rofecoxib), SD-8381, 4-Methyl-2-(3,4-dimethylphenyl)-1-(4-sulfamoyl-phenyl-IH-pyrrole, T-614, JTE-522, S-2474, SVT-2016, CT-3, SC-58125 and Arcoxia (etoricoxib).

Examples of non-steroidal anti-inflammatory drugs (NSAIDs) include, but are not limited to, Salsalate (Amigesic), Diflunisal (Dolobid), Ibuprofen (Motrin), Ketoprofen (Orudis), Nabumetone (Relafen), Piroxicam (Feldene), Naproxen (Aleve, Naprosyn), Diclofenac (Voltaren), Indomethacin (Indocin), Sulindac (Clinoril), Tolmetin (Tolectin), Etodolac (Lodine), Ketorolac (Toradol) and Oxaprozin (Daypro).

Examples of ErbB2 receptor inhibitors include, but are not limited to, CP-724-714, CI-1033, (canertinib), Herceptin (trastuzumab), Omitarg (2C4, petuzumab), TAK-165, GW-572016 (Ionafarnib), GW-282974, EKB-569, PI-166, dHER2 (HER2 Vaccine), APC8024 (HER2 Vaccine), anti-HER2neu bispecific antibody, B7.her2IgG3, AS HER2 trifunctional bispecfic antibodies, mAB AR-209 and mAB 2B-1.

Examples of alkylating agents include, but are not limited to, nitrogen mustard N-oxide, cyclophosphamide, ifosfamide, trofosfamide, Chlorambucil, melphalan, busulfan, mitobronitol, carboquone, thiotepa, ranimustine, nimustine, temozolomide, AMD-473, altretamine, AP-5280, apaziquone, brostallicin, bendamustine, carmustine, estramustine, fotemustine, glufosfamide, KW-2170, mafosfamide, and mitolactol, carmustine (BCNU), lomustine (CCNU), Busulfan, Treosulfan, Decarbazine and Temozolomide.

Examples of antimetabolites include but are not limited to, methotrexate, 6-mercaptopurine riboside, mercaptopurine, uracil analogues such as 5-fluorouracil (5-FU) alone or in combination with leucovorin, tegafur, UFT, doxifluridine, carmofur, cytarabine, cytarabine ocfosate, enocitabine, S-I, Alimta (premetrexed disodium, LY231514, MTA), Gemzar (gemcitabine), fludarabine, 5-azacitidine, capecitabine, cladribine, clofarabine, decitabine, eflornithine, ethnylcytidine, cytosine arabinoside, hydroxyurea, TS-I, melphalan, nelarabine, nolatrexed, ocfosate, disodium premetrexed, pentostatin, pelitrexol, raltitrexed, triapine, trimetrexate, vidarabine, vincristine, vinorelbine, mycophenolic acid, tiazofurin, Ribavirin, EICAR, hydroxyurea and deferoxamine.

Examples of antibiotics include intercalating antibiotics but are not limited to, aclarubicin, actinomycins such as actinomycin D, amrubicin, annamycin, adriamycin, bleomycin a, bleomycin b, daunorubicin, doxorubicin, elsamitrucin, epirbucin, glarbuicin, idarubicin, mitomycin C, nemorubicin, neocarzinostatin, peplomycin, pirarubicin, rebeccamycin, stimalamer, streptozocin, valrubicin, zinostatin and combinations thereof.

Examples of topoisomerase inhibiting agents include, but are not limited to, one or more agents selected from the group consisting of aclarubicin, amonafide, belotecan, camptothecin, 10-hydroxycamptothecin, 9-aminocamptothecin, diflomotecan, irinotecan HCL (Camptosar), edotecarin, epirubicin (Ellence), etoposide, exatecan, gimatecan, lurtotecan, orathecin (Supergen), BN-80915, mitoxantrone, pirarbucin, pixantrone, rubitecan, sobuzoxane, SN-38, tafluposide and topotecan.

Examples of antibodies include, but are not limited to, Rituximab, Cetuximab,

Bevacizumab, Trastuzimab, specific CD40 antibodies and specific IGFIR antibodies.

Examples of hormonal therapies include, but are not limited to, exemestane (Aromasin), leuprolide acetate, anastrozole (Arimidex), fosrelin (Zoladex), goserelin, doxercalciferol, fadrozole, formestane, tamoxifen citrate (tamoxifen), Casodex, Abarelix, Trelstar, finasteride, fulvestrant, toremifene, raloxifene, lasofoxifene, letrozole, flutamide, bicalutamide, megesterol, mifepristone, nilutamide, dexamethasone, predisone and other glucocorticoids.

Examples of retinoidsdeltoids include, but are not limited to, seocalcitol (EB 1089, CB 1093), lexacalcitrol (KH 1060), fenretinide, Aliretinoin, Bexarotene and LGD-1550.

Examples of plant alkaloids include, but are not limited to, vincristine, vinblastine, vindesine and vinorelbine.

Examples of proteasome inhibitors include, but are not limited to, bortezomib (Velcade), MGI 32, NPI-0052 and PR-171.

Examples of immunologicals include, but are not limited to, interferons and numerous other immune enhancing agents. Interferons include interferon alpha, interferon alpha-2a, interferon, alpha-2b, interferon beta, interferon gamma-1a, interferon gamma-1b (Actimmune), or interferon gamma-nl and combinations thereof. Other agents include filgrastim, lentinan, sizofilan, TheraCys, ubenimex, WF-10, aldesleukin, alemtuzumab, BAM-002, decarbazine, daclizumab, denileukin, gemtuzumab ozogamicin, ibritumomab, imiquimod, lenograstim, lentinan, melanoma vaccine (Corixa), molgramostim, OncoVAC-CL, sargaramostim, tasonermin, tecleukin, thymalasin, tositumomab, Virulizin, Z-100, epratuzumab, mitumomab, oregovomab, pemtumomab (Y-muHMFGI), Provenge (Dendreon), CTLA4 (cytotoxic lymphocyte antigen 4) antibodies and agents capable of blocking CTLA4 such as MDX-010.

Examples of biological response modifiers are agents that modify defense mechanisms of living organisms or biological responses, such as survival, growth, or differentiation of tissue cells to direct them to have anti-tumor activity. Such agents include krestin, lentinan, sizofrran, picibanil and ubenimex.

Examples of pyrimidine analogs include, but are not limited to, 5-Fluorouracil,

Floxuridine, Doxifluridine, Ratitrexed, cytarabine (ara C), Cytosine arabinoside, Fludarabine, and Gemcitabine.

Examples of purine analogs include but are not limited to, Mercaptopurine and thioguanine.

Examples of antimitotic agents include, but are not limited to, ABT-751, paclitaxel, docetaxel, epothilone D (KOS-862) and ZK-EPO.

Compounds of the present invention are also intended to be used as a radiosensitizer that enhances the efficacy of radiotherapy. Examples of radiotherapy include but are not limited to, external beam radiotherapy (XBRT), or teletherapy, brachtherapy or sealed source radiotherapy, unsealed source radiotherapy.

In addition to treating cancer and sensitizing a cancer cell to the cytotoxic effect of radiotherapy and chemotherapy, compounds of the present invention are useful in methods of treating diseases, conditions, and injuries to the central nervous system, such as neurological diseases, neurodegenerative disorders, and traumatic brain injuries. The neurological disease treated is Huntington's disease, Parkinson's disease, Alzheimer's disease, spinal muscular atrophy, lupus, or schizophrenia.

Another potential use of compounds of the present invention is to treat parasite infections (e.g., *Plasmodium* infection).

The present compounds can be a racemic mixture or have S- or R-configuration at the stereogenic centers when applicable. References to a compound of Formula I in this specification, including the accompanying claims, unless otherwise specified, embrace each of the enantiomers and racemic and scalemic mixtures of the stereoisomers.

The invention also encompasses a pharmaceutical composition comprising a compound of Formula I or its prodrug and a pharmaceutically acceptable carrier.

One or more than one of the protons in compounds of Formula I can be replaced with deuterium atom(s), thus providing deuterated analogs that may have improved pharmacological activities The compounds described here may be administered at a conventional dosage levels. Suitable dosage levels will be about 0.001 to 50 mg/kg per day, preferably 0.005 to 30 mg/kg per day, and especially 0.05 to 10 mg/kg per day. The compound may be administered on a regimen of once, twice, or three times per day via oral, IV infusion, subcutaneous injection, or topical application, or in the form of suppositories for rectal administration.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients.

It will be understood that in the discussion of methods of treatment which follows, references to the compounds of Formula I are meant to also include the pharmaceutically acceptable salts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and U.S. Pat. No. 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethyl-cellulose, methylcellulose, hydroxypropylmethy-cellulose, sulfo-alky cyclodextrins, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative, flavoring and coloring agent. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of Formula I are employed. (For purposes of this application, topical application shall include mouth washes and gargles.)

Dosage levels of the order of from about 0.01 mg to about 140 mg/kg of body weight per day are useful in the treatment of the above-indicated conditions, or alternatively about 0.5 mg to about 7 g per patient per day. For example, patients may be effectively treated by the administration of from about 0.01 to 50 mg of the compound per kilogram of body weight per day, or alternatively about 0.5 mg to about 3.5 g per patient per day, preferably 2.5 mg to 1 g per patient per day.

The amount of active ingredient that may be combined with the carrier materials to produce a single dosage form will vary depending upon the host treated and the particular mode of administration. For example, a formulation intended for the oral administration of humans may contain from 0.5 mg to 5 g of active agent compounded with an appropriate and convenient amount of carrier material which may vary from about 5 to about 95 percent of the total composition. Dosage unit forms will generally contain between from about 1 mg to about 1000 mg of an active ingredient, typically 25 mg, 50 mg, 100 mg, 200 mg, 300 mg, 400 mg, 500 mg, 600 mg, 800 mg, or 1000 mg.

It will be understood, however, that the specific dose level for any particular patient will depend upon a variety of factors including the age, body weight, general health, sex, diet, time of administration, route of administration, rate of excretion, drug combination and the severity of the particular disease undergoing therapy.

Synthetic Methods

The compounds of the present invention can be prepared according to the following synthetic schemes.

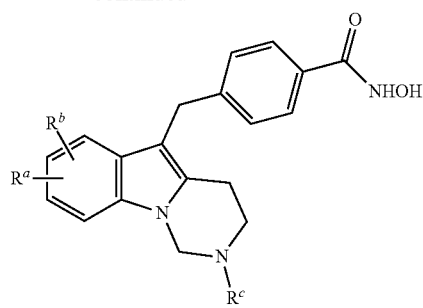

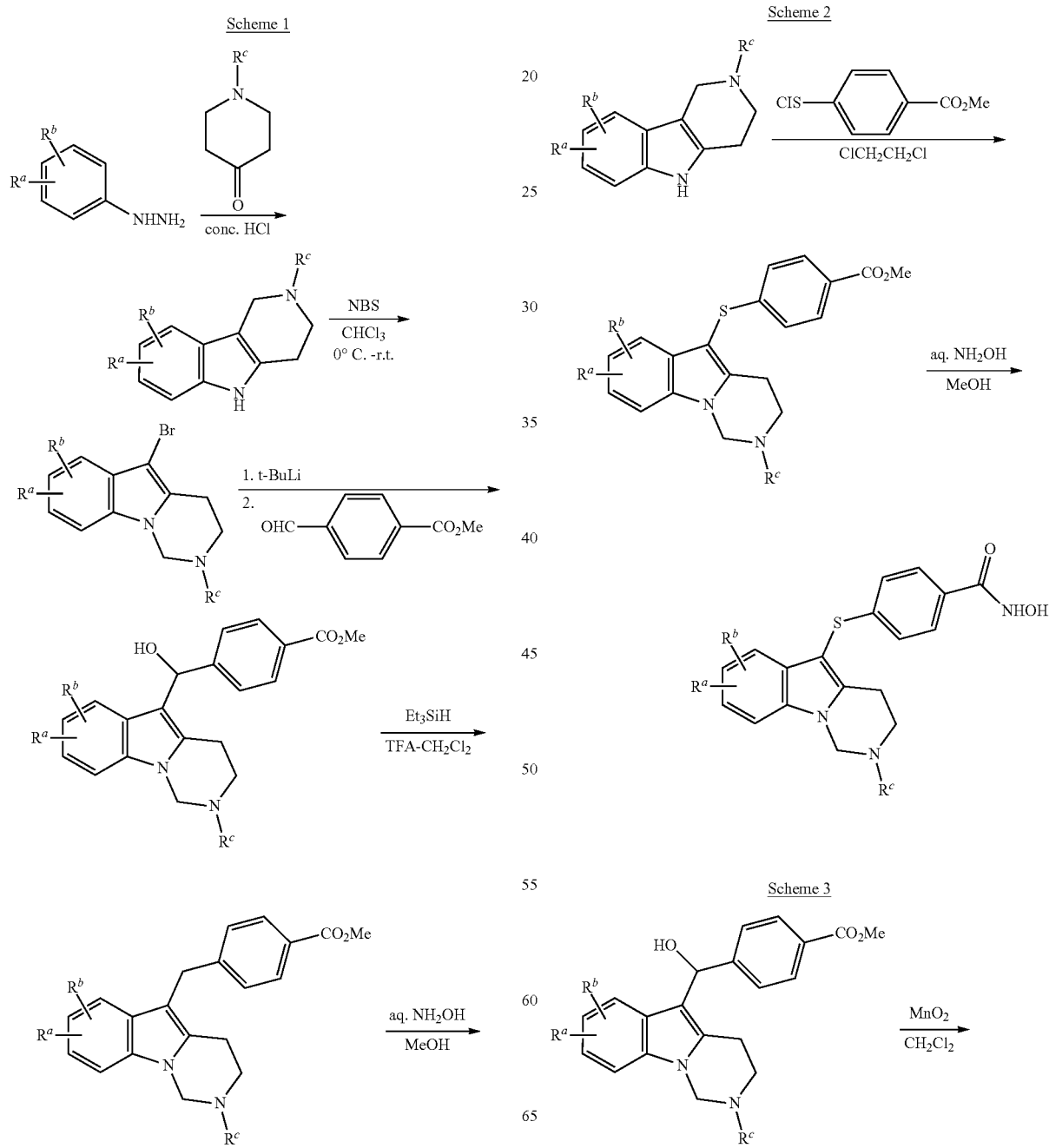

33
-continued
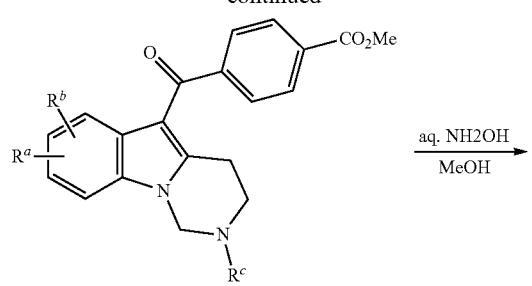
34
-continued
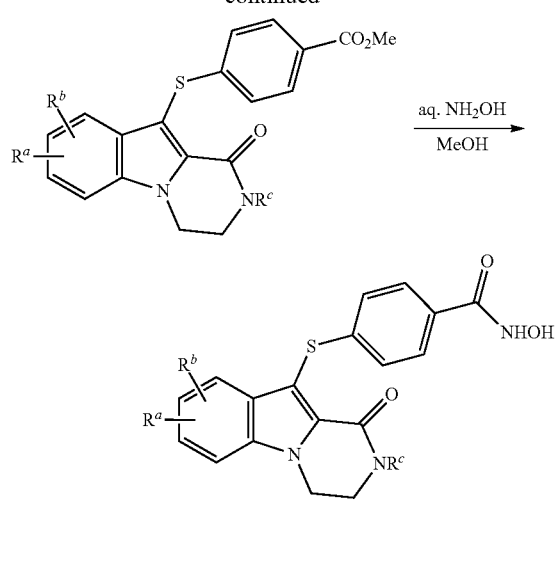
Scheme 4
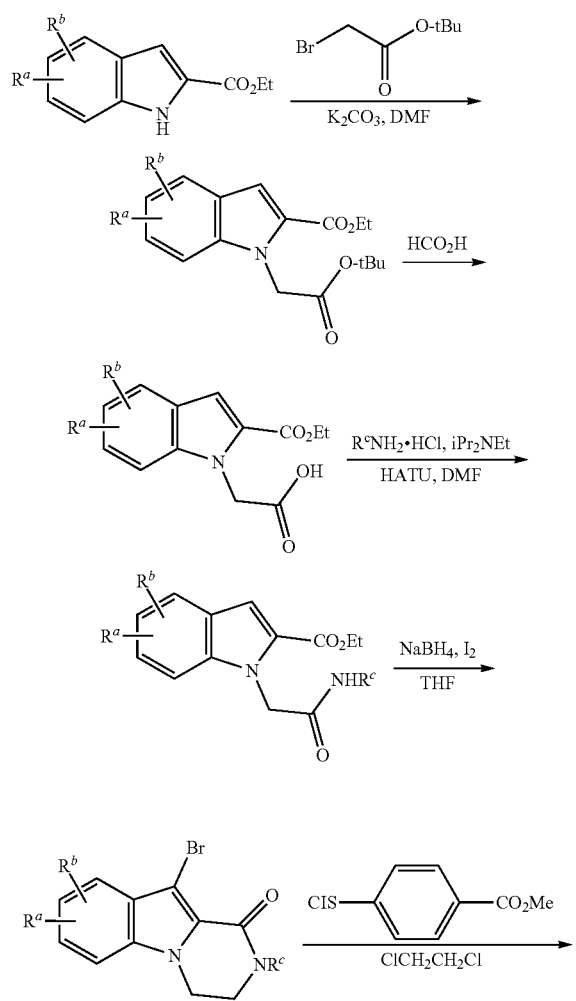
Scheme 5
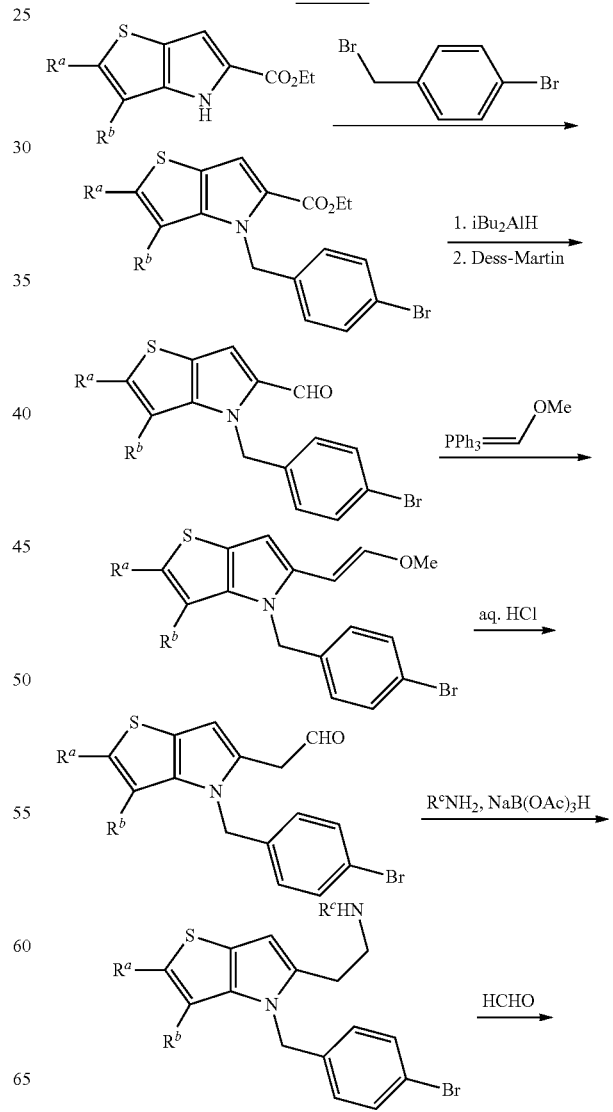

-continued

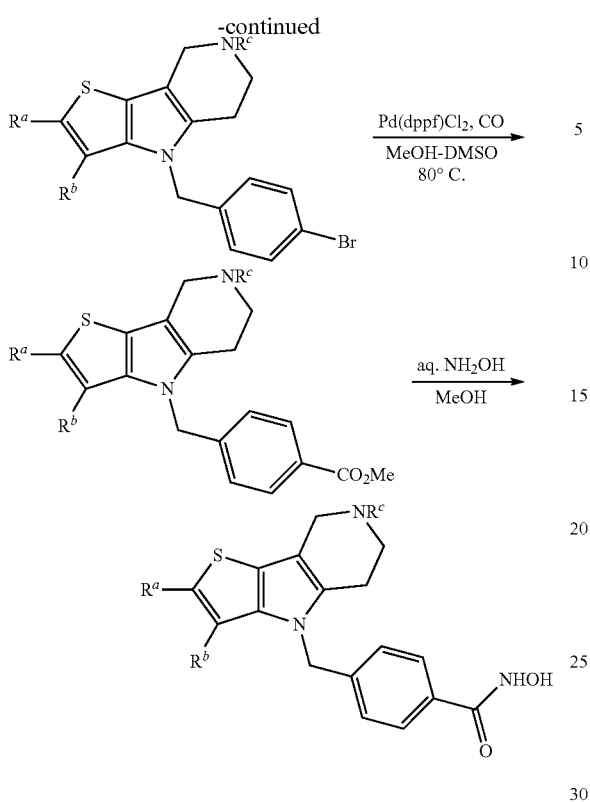

Synthesis

Compounds of the present invention may be made by synthetic chemical processes described in Scheme 1-5, examples of which are shown herein below. It is meant to be understood that the order of the steps in the processes may be varied, that reagents, solvents and reaction conditions may be substituted for those specifically mentioned, and that vulnerable moieties may be protected and deprotected, as necessary. Unless otherwise indicated, starting materials are either commercially available or readily accessible through laboratory synthesis by anyone reasonably familiar with the art.

The following abbreviations have the meanings indicated. DBU means 1,8-diazabicyclo[5.4.0]undec-7-ene; DIBAL means diisobutylaluminum hydride; DIEA means diisopropylethylamine; DMAP means N,N-dimethylaminopyridine; DME means 1,2-dimethoxyethane; DMF means N,N-dimethylformamide; dmpe means 1,2-bis(dimethylphosphino)ethane, DMSO means dimethylsulfoxide; dppb means 1,4-bis(diphenylphosphino)butane; dppe means 1,2-bis(diphenylphosphino)ethane; dppf means 1,r-bis(diphenylphosphino)ferrocene; dppm means 1,l-bis(diphenylphosphino)methane; EDCI means 1-(3-dimethylaminopropyl)-3-ethylcarbodiimide; HATU means O-(7-azabenzotriazol-l-yl)-N,NTSr'N'-tetramethyluronium hexafluorophosphate; HMPA means hexamethylphosphorarnide; IPA means isopropyl alcohol; LDA means lithium diisopropylamide; LHMDS means lithium bis(hexamethyldisilylamide); LAH means lithium aluminum hydride; NCS means N-chlorosuccinimide; PyBOP means benzotriazol-1-yloxytripyrrolidinophosphonium hexafluorophosphate; TDA-I means tris(2-(2-methoxyethoxy)ethyl)amine; TEA means triethylamine; TFA means trifluoroacetic acid; THF means tetrahydrofuran; NCS means N-chlorosuccinimide; NMM means N-methylmorpholine; NMP means N-methylpyrrolidine; PPh3 means triphenylphosphine.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

Example 1

N-Hydroxy-4-((2-methyl-1,2,3,4-tetrahydropyrimido[1,6-a]indol-5-yl)thio)benzamide

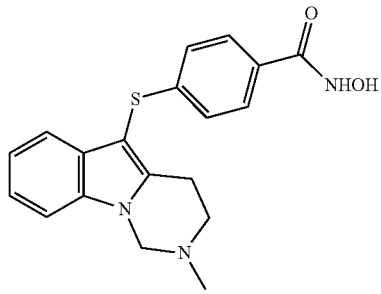

Step 1
2-methyl-2,3,4,5-tetrahydro-1H-pyrido[4,3-b]indole

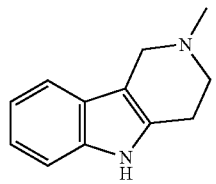

To a suspension of phenylhydrazine (5.4 g) in 75 mL water was added slowly 4.2 mL of 12 N HCl, followed by addition of 1-methylpiperidin-4-one (6.7 g). Additional 16 g of 12N HCl was added and the reaction mixture was heated at 55° C. for 2 days. After cooling in a ice-water bath, 10 N NaOH solution was added slowly until pH>12.20 g of NaCl was added to the mixture and the reaction mixture was extracted with 2×100 mL of CH2Cl2. The combined extracts were dried over Na2SO4, filtered and concentrated. The residue was swished from EtOAc to give 7 g of the title compounds as a light yellow solid.

Step 2 methyl 4-((2-methyl-1,2,3,4-tetrahydropyrimido[1,6-a]indol-5-yl)thio)benzoate

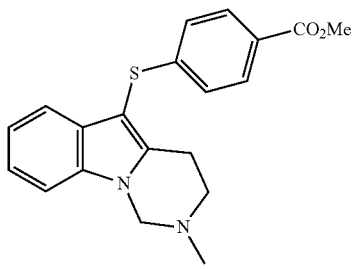 [SMILES: COC(=O)c1ccc(Sc2c3n(c4ccccc24)CN(C)CC3)cc1]

$^1$H NMR (300 MHz, acetone-d$_6$) δ 9.88 (bs, 1H), 7.33 (d, 1H), 7.28 (d, 1H), 6.42-7.05 (m, 2H), 3.55 (t, 2H), 2.80-2.88 (m, 2H), 2.70-2.77 (m, 2H), 2.46 (s, 3H).

Step 2 methyl 4-((2-methyl-1,2,3,4-tetrahydropyrimido[1,6-a]indol-5-yl)thio)benzoate

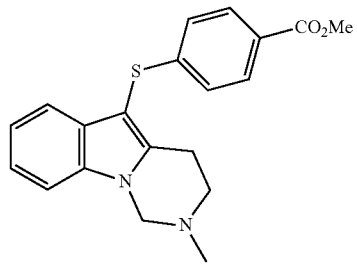 [SMILES: COC(=O)c1ccc(Sc2c3n(c4ccccc24)CN(C)CC3)cc1]

To a solution of dimethyl 4,4'-disulfanediyldibenzoate (0.34 g) in 6 mL of ClCH$_2$CH$_2$Cl cooled at 0° C. was added dropwise 0.081 mL of SO$_2$Cl$_2$ over 2 min. The reaction mixture was stirred for 1 h at 0° C., and then transferred via a syringe to solution of 2-methyl-2,3,4,5-tetrahydro-1H-pyrido[4,3-b]indole (0.19 g) in 6 mL of DMF at room temperature. After stirring for 10 min, the reaction was quenched with 10 mL of saturated aqueous solution of NaHCO$_3$ and the reaction mixture was extracted 50 mL of EtOAc. The extract was dried over Na$_2$SO$_4$, filtered and concentrated. The residue was purified by silica gel chromatography eluted with up to 80% EtOAc/hexanes to give 0.2 g of the title product as beige solid.

$^1$H NMR (300 MHz, CDCl3): δ 7.80 (d, 2H), 7.55 (d, 2H), 7.12-32 (m, 3H), 7.05 (d, 2H), 4.80 (s, 2H), 3.85 (s, 3H), 2.96-3.10 (m, 4H), 2.60 (s, 3H).

Step 3 N-Hydroxy-4-((2-methyl-1,2,3,4-tetrahydropyrimido[1,6-a]indol-5-yl)thio)benzamide

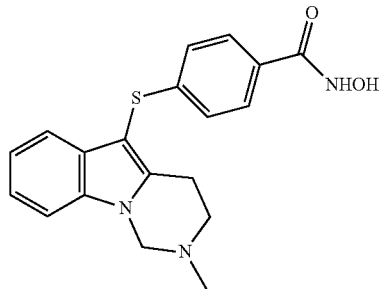

To a solution of methyl 4-((2-methyl-1,2,3,4-tetrahydropyrimido[1,6-a]indol-5-yl)thio)benzoate (0.4 g) and NH2OH.HCl (0.63 g) in 4 mL of dry MeOH was added 2.5 mL of 25% NaOMe solution in methanol. The reaction mixture was stirred for 4 h at r.t. and then quenched with 10 mL of potassium phosphate buffer solution. The mixture was extracted 40 mL of EtOAc. The extract was dried over Na2SO4, filtered and concentrated. The residue was purified by silica gel chromatography eluted with up to 10% MeOH/CH2Cl2 to give 0.12 g of the title product as white solid.

$^1$H NMR (300 MHz, acetone-d6) δ 7.66 (d, 2H), 7.47 (m, 2H), 7.22 (t, 1H), 7.12 (t, 1H), 7.08 (d, 2H), 4.90 (s, 2H), 3.06 (s, 4H), 2.60 (s, 3H).

Example 2

4-((2,7-Dimethyl-1,2,3,4-tetrahydropyrimido[1,6-a]indol-5-yl)thio)-N-hydroxybenzamide

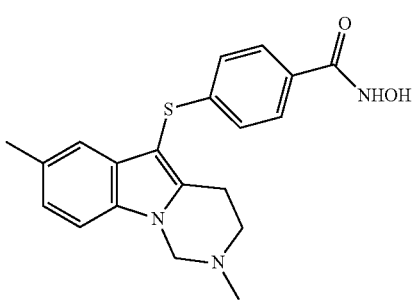

The title compound was prepared from 2,8-dimethyl-2,3,4,5-tetrahydro-1H-pyrido[4,3-b]indole by following the reaction procedures described in EXAMPLE 1.

$^1$H NMR (300 MHz, CDCl$_3$): δ 7.46 (d, 2H), 7.32 (s, 1H), 7.21 (d, 1H), 7.07 (d, 1H), 7.00 (d, 2H), 4.80 (s, 2H), 2.96-3.06 (m, 4H), 2.60 (s, 3H), 2.43 (s, 3H).

Example 3

N-hydroxy-4-((2-methyl-1,2,3,4-tetrahydropyrimido[1,6-a]indol-5-yl)methyl)benzamide

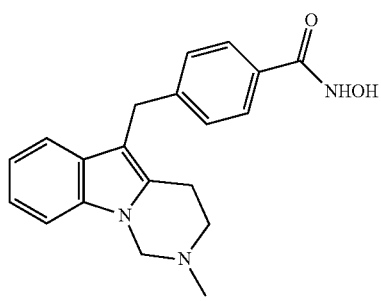

Step 1 5-bromo-2-methyl-1,2,3,4-tetrahydropyrimido[1,6-a]indole

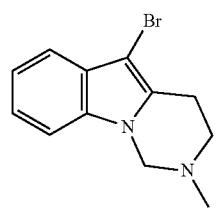

To a solution of 2-methyl-2,3,4,5-tetrahydro-1H-pyrido[4, 3-b]indole (3.7 g) in 40 mL of CHCl$_3$ cooled at 0° C. was added 4 g of NBS in two portions. After stirring for 2 h at r.t., the reaction mixture was treated with 30 mL of water and 20 mL of saturated aqueous solution of NaHCO$_3$, and then extracted with 200 mL of CH$_2$Cl$_2$. The extract was dried over Na$_2$SO$_4$ for 2 days, and then filtered through a pad of silica gel, concentrated to give 4 g of the title compound as a light brown solid.

$^1$H NMR (300 MHz, CDCl$_3$): δ 7.53 (m, 1H), 7.08-7.18 (m, 3H), 4.75 (s, 2H), 2.96-3.08 (m, 4H), 2.60 (s, 3H).

Step 2 methyl 4-(hydroxy(2-methyl-1,2,3,4-tetrahydropyrimido[1,6-a]indol-5-yl)methyl)benzoate

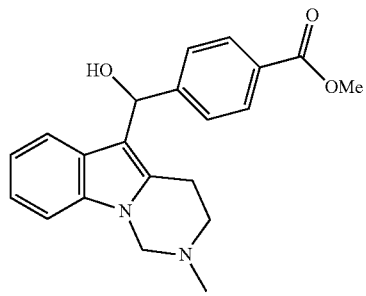 [SMILES: COC(=O)c1ccc(C(O)c2c3n(c4ccccc24)CN(C)CC3)cc1]

To a solution of 5-bromo-2-methyl-1,2,3,4-tetrahydropyrimido[1,6-a]indole (0.254 g) in 8 mL of ether cooled at −78° C. was added t-BuLi (1.4 mL, 1.7 M in pentane) dropwise. After attiring at −78° C. for 15 min, a solution of methyl 4-formylbenzoate (0.200 g in 2 mL of ether) was added quickly by a syringe. The reaction mixture was wormed to r.t. over 10 min, and quenched with 10 mL of saturated aqueous solution of NH4Cl, and 20 mL of EtOAc was added. The solid was collected by filtration to give 0.2 g of the title compound as a white solid.

$^1$H NMR (300 MHz, DMSO-d$_6$): δ 7.90 (d, 2H), 7.65 (d, 2H), 7.34 (d, 1H), 7.30 (d, 1H), 7.00 (t, 3H), 6.88 (t, 1H), 6.06 (s, 1H), 4.70 (d, 1H), 4.65 (d, 1H), 3.80 (s, 3H), 2.90 (m, 4H), 2.45 (s, 3H).

Step 3 methyl 4-((2-methyl-1,2,3,4-tetrahydropyrimido[1,6-a]indol-5-yl)methyl)benzoate

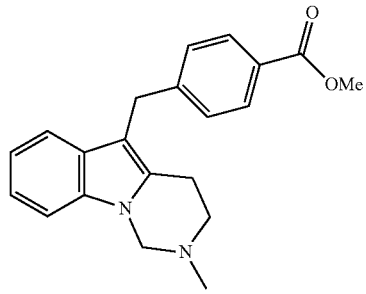 [SMILES: COC(=O)c1ccc(Cc2c3n(c4ccccc24)CN(C)CC3)cc1]

To a solution of methyl 4-(hydroxy(2-methyl-1,2,3,4-tetrahydropyrimido[1,6-a]indol-5-yl)methyl)benzoate (80 mg) and Et3SiH (0.5 mL) in 5 mL of CH2Cl2 was added 0.1 mL of TFA. After stirring for 10 min at r.t., the reaction mixture was poured into 15 mL of saturated aqueous solution of NaHCO3 and the mixture was extracted with 2×20 mL of EtOAc. The combined extracts were dried over Na2SO4, filtered, and concentrated. The residue was purified by silica gel chromatography eluted with up to 100% EtOAc/hexanes to give 70 mg of the title product as white solid.

Step 4 N-hydroxy-4-((2-methyl-1,2,3,4-tetrahydropyrimido[1,6-a]indol-5-yl)methyl)benzamide

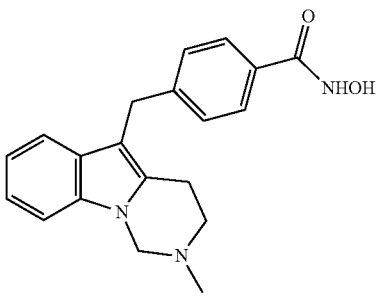

A solution of methyl 4-((2-methyl-1,2,3,4-tetrahydropyrimido[1,6-a]indol-5-yl)methyl)benzoate (0.07 g) and 1 mL of 50% aqueous solution of NH2OH in 3 mL of MeOH was stirred at r.t. for 12 h, and the reaction mixture was concentrated under vacuum. The residue was purified by silica gel chromatography eluted with up to 10% MeOH/CH2Cl2 to give 0.02 g of the title product as white solid.

1H NMR (300 MHz, DMSO-d6) δ 7.76 (d, 1H), 7.58 (d, 2H), 7.32 (d, 1H), 7.25 (d, 3H), 7.08 (t, 1H), 6.96 (t, 1H), 4.70 (s, 2H), 4.05 (s, 2H), 2.90-3.05 (m, 4H), 2.54 (s, 3H).

Example 4

N-hydroxy-4-(2-methyl-1,2,3,4-tetrahydropyrimido[1,6-a]indole-5-carbonyl)benzamide

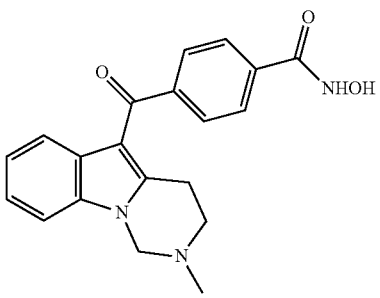

Step 1 methyl 4-(2-methyl-1,2,3,4-tetrahydropyrimido[1,6-a]indole-5-carbonyl)benzoate

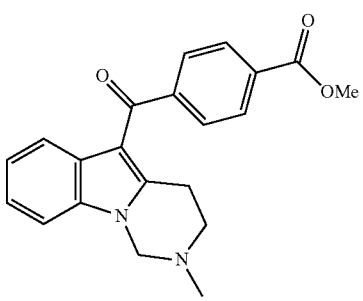 [SMILES: COC(=O)c1ccc(C(=O)c2c3n(c4ccccc24)CN(C)CC3)cc1]

To a solution of methyl 4-(hydroxy(2-methyl-1,2,3,4-tetrahydropyrimido[1,6-a]indol-5-yl)methyl)benzoate (400 mg) in 60 mL of CH$_2$Cl$_2$ was added 0.5 g of Dess-Martin reagent. After stirring for 10 min at r.t., the reaction was quenched with 25 mL of saturated aqueous solution of NaHCO3 and the CH$_2$Cl$_2$ phase was dried over Na$_2$SO$_4$, filtered, and concentrated. The residue was purified by silica gel chromatography eluted with up to 10% MeOH/EtOAc to give 80 mg of the title product as white solid.

$^1$H NMR (300 MHz, acetone-d$_6$) δ 8.12 (d, 2H), 7.64 (d, 2H), 7.42 (d, 2H), 7.18 (t, 1H), 7.12 (t5, 1H), 4.90 (s, 2H), 3.94 (s, 3H), 3.05 (m, 2H), 2.96 (m, 2H), 2.56 (s, 3H).

Step 2 4-(2-methyl-1,2,3,4-tetrahydropyrimido[1,6-a]indole-5-carbonyl)benzoic acid

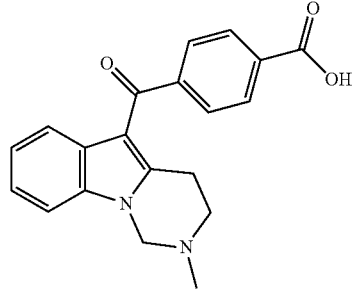 [SMILES: CN1CCc2c(C(=O)c3ccc(C(=O)O)cc3)c3ccccc3n2C1]

To a solution of methyl 4-(2-methyl-1,2,3,4-tetrahydropyrimido[1,6-a]indole-5-carbonyl)benzoate (80 mg) in 1 mL of MeOH, 2 mL of THF and 1 mL of water was added 0.2 mL of 2N NaOH. After stirring for 0.5 h, the reaction mixture was treated with 5 mL of pH7 potassium phosphate buffer, extracted with 4×20 mL of EtOAc. The combined extracts were dried over Na2SO4, filtered, and concentrated to give the crude title compound which was used for the next step without further purification.

Step 3 N-hydroxy-4-(2-methyl-1,2,3,4-tetrahydropyrimido[1,6-a]indole-5-carbonyl)benzamide

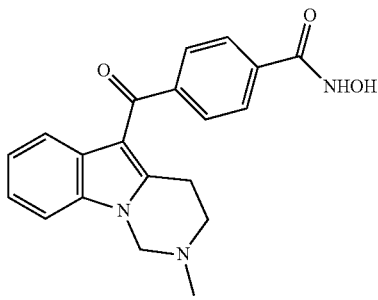

To a solution of 4-(2-methyl-1,2,3,4-tetrahydropyrimido[1,6-a]indole-5-carbonyl)benzoic acid (60 mg) in 4 mL of DMF was added 100 mg of carbonyldiimidazole (CDI). The reaction mixture was stirred at 40° C. for 1 h and then treated with 280 mg of NH$_2$OH.HCl, followed by 0.6 mL of Et$_3$N. After stirring for 20 min at r.t., 5 mL of pH7 potassium phosphate buffer and 10 mL of brine were added and reaction mixture was extracted with 3×20 mL of EtOAc. The combined extracts were dried over Na$_2$SO$_4$, filtered, and the residue was purified by silica gel chromatography eluted with up to 10% MeOH/CH$_2$Cl$_2$ to give 10 mg of the title product as white solid.

$^1$H NMR (300 MHz, CD$_3$OD) δ 7.87 (d, 2H), 7.69 (d, 2H), 7.42 (d, 1H), 7.30 (d, 1H), 7.21 (t, 1H), 7.09 (t, 1H), 4.89 (s, 2H), 3.13 (t, 2H), 2.99 (t, 2H), 2.58 (s, 3H).

Example 5

N-hydroxy-4-((2-methyl-1-oxo-1,2,3,4-tetrahydropyrazino[1,2-a]indol-10-yl)thio)benzamide

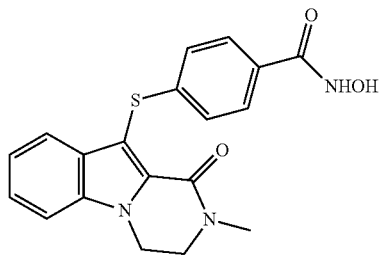

Step 1 ethyl 1-(2-tert-butoxy-2-oxoethyl)-1H-indole-2-carboxylate

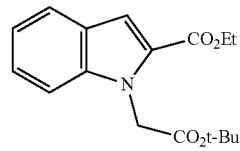 [SMILES: CCOC(=O)c1cc2ccccc2n1CC(=O)OC(C)(C)C]

A mixture of ethyl 1H-indole-2-carboxylate (5.68 g, 30 mmol), tert-butyl 2-bromoacetate (6.44 g, 33 mmol), and potassium carbonate in 60 mL of DMF was heated to 80° C. for 2 days. The TLC showed that the reaction stopped at around 50% completion. The reaction was worked up by the addition of water and the aqueous phase was extracted with EtOAc (2×30 mL). The combined organic phase was washed with brine, dried over Na$_2$SO$_4$, filtered and evaporated. The residue was purified by Combiflash (40 g silica gel cartridge, 0-30% EtOAc in hexane) to afford the desired product.

$^1$H NMR (300 MHz, acetone-d$_6$) δ 7.72 (d, 1H), 7.51 (d, 1H), 7.33 (d, 1H), 7.30 (s, 1H), 7.16 (t, 1H), 5.30 (s, 2H), 4.32 (q, 2H), 1.43 (s, 9H), 1.40 (t, 3H).

Step 2 2-(2-(ethoxycarbonyl)-1H-indol-1-yl)acetic acid

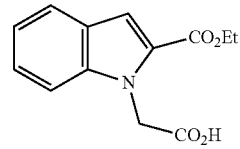 [SMILES: CCOC(=O)c1cc2ccccc2n1CC(=O)O]

A solution of ethyl 1-(2-tert-butoxy-2-oxoethyl)-1H-indole-2-carboxylate (4.64 g) is 25 mL of formic acid (88%) was heated at 100° C. for 1 hr. TLC showed that the reaction was complete. The solvent was removed by evaporation and the residue was triturated with water and filtered to collect the solid. The beige solid was air dried overnight to afford 3.78 g of the desired product.

$^1$H NMR (300 MHz, acetone-$d_6$) δ 7.74 (d, 1H), 7.57 (d, 1H), 7.37 (t, 1H), 7.30 (s, 1H), 7.18 (t, 1H), 5.42 (s, 2H), 4.31 (q, 2H), 1.37 (t, 3H).

Step 3 ethyl 1-(2-(methylamino)-2-oxoethyl)-1H-indole-2-carboxylate

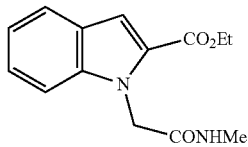

A mixture of 2-(2-(ethoxycarbonyl)-1H-indol-1-yl)acetic acid (3.78 g), HATU (6.98 g), methylammonium chloride, and Hunig's base (6.33 mL) in DMF (77 mL) was stirred at room temperature for 24 hr. The reaction was worked up by the addition of water and the aqueous phase was extracted with EtOAc (2×65 mL). The combined organic phase was washed with brine, dried over Na$_2$SO$_4$, filtered and evaporated. The residue was purified by CombiFlash (0-100% EtOAc/hexane) to afford the title compound as a yellowish solid.

$^1$H NMR (300 MHz, acetone-$d_6$) δ 7.71 (d, 1H), 7.46 (d, 1H), 7.35 (t, 1H), 7.30 (s, 1H), 7.16 (t, 1H), 6.98 (bs, 1H), 5.23 (s, 2H), 4.33 (q, 2H), 2.68 (d, 3H), 1.39 (t, 3H).

Step 4
2-methyl-3,4-dihydropyrazino[1,2-a]indol-1(2H)-one

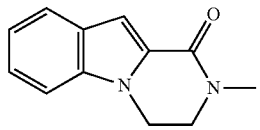

To a mixture of ethyl 1-(2-(methylamino)-2-oxoethyl)-1H-indole-2-carboxylate (0.86 g), NaBH$_4$ (0.39 g) in 33 mL of THF stirred at 0° C. under a N2 atmosphere, a solution of Iodine (1.26 g, 10 mL THF) was added dropwise. The resulting mixture was reacted at 65° C. for 24 hr. The reaction was worked up by the addition of HCl (con., 1.5 mL) and heated at 65° C. for 4 hr. Then the mixture was neutralized by saturated NaHCO$_3$ solution and the aqueous phase was extracted with EtOAc (2×60 mL). The combined organic phase was washed with brine, dried over Na$_2$SO$_4$, filtered and evaporated. The residue was purified by Combiflash (0-100% EtOAc/hexane) to afforded 208 mg of the title compound.

$^1$H NMR (300 MHz, acetone-$d_6$) δ 7.68 (d, 1H), 7.46 (d, 1H), 7.30 (t, 1H), 7.13 (t, 1H), 7.10 (s, 1H), 4.40 (t, 2H), 3.88 (t, 2H), 3.10 (s, 3H).

Step 5 methyl 4-((2-methyl-1-oxo-1,2,3,4-tetrahydropyrazino[1,2-a]indol-10-yl)thio)benzoate

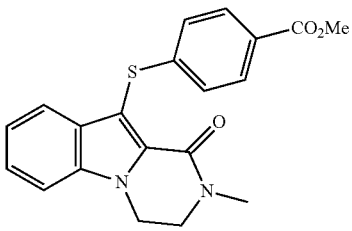 [SMILES: COC(=O)c1ccc(Sc2c3n(c4ccccc24)CCN(C)C3=O)cc1]

To a solution of dimethyl 4,4'-disulfanediyldibenzoate (0.5 g) in 6 mL of ClCH$_2$CH$_2$Cl cooled at 0° C. was added dropwise 0.122 mL of SO$_2$Cl$_2$ over 2 min. The reaction mixture was stirred for 1 h at 0° C., and then transferred via a syringe to a solution of 2-methyl-3,4-dihydropyrazino[1,2-a]indol-1(2H)-one (0.25 g) in 6 mL of DMF at room temperature. After stirring for 30 min, the reaction was quenched with 10 mL of saturated aqueous solution of NaHCO$_3$ and the reaction mixture was extracted with 50 mL of EtOAc. The extract was dried over Na$_2$SO$_4$, filtered and concentrated. The residue was purified by silica gel chromatography eluted with up to 100% EtOAc/hexanes to give 0.25 g of the title product as beige solid which was contaminated with an impurity. The impure product was used for the next step without further purification.

Step 6 N-hydroxy-4-((2-methyl-1-oxo-1,2,3,4-tetrahydropyrazino[1,2-a]indol-10-yl)thio)benzamide

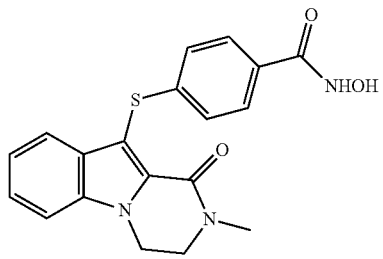

To a solution of methyl 4-((2-methyl-1-oxo-1,2,3,4-tetrahydropyrazino[1,2-a]indol-10-yl)thio)benzoate (0.25 g, impure) and NH$_2$OH.HCl (0.35 g) in 4 mL of dry MeOH was added 1.4 mL of 25% NaOMe solution in methanol. The reaction mixture was stirred for 20 min at r.t. and 0.3 mL of more 25% NaOMe solution in methanol was added. After stirring for 2 h, the reaction mixture was quenched with 10 mL of potassium phosphate buffer solution. The mixture was extracted with 2×30 mL of EtOAc. The combined extracts were dried over Na$_2$SO$_4$, filtered and concentrated. The residue was purified by silica gel chromatography eluted with up to 10% MeOH/CH$_2$Cl$_2$ to give 0.097 g of the title product as beige solid.

$^1$H NMR (300 MHz, CD$_3$OD) δ 7.65 (d, 2H), 7.62 (d, 1H), 7.55 (d, 1H), 7.46 (t, 1H), 7.22 (t, 1H), 7.10 (d, 2H), 4.50 (m, 2H), 3.97 (m, 2H), 3.14 (s, 3H).

Biochemical Evaluation

The compounds of the present invention were tested for inhibition of human HDAC6 at Reaction Biology Corporation by using 50 μM Fluorogenic peptide from p53 residues 379-382 (RHKKAc) as the substrate. The $IC_{50}$s of the compounds of the present invention are shown in Table 1:

TABLE 1

| HDAC6 inhibition data for Example 1-5 | | | | | |
|---|---|---|---|---|---|
| Compound | Example 1 | Example 2 | Example 3 | Example 4 | Example 5 |
| $IC_{50}$, nM | 2.48 | 35.5 | 10.7 | 1490 | 1.76 |

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A compound of Formula I

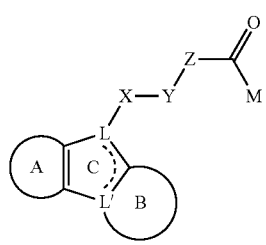

Formula I or a pharmaceutically acceptable salt thereof, wherein:
L and L' are selected from a nitrogen atom or carbon atom with the proviso that L and L' are a different atom;
X is O, S, $CH_2$, C(O), or a bond with the proviso that X is different than O and S when L is a nitrogen atom;
Y is a bond, an aryl, or a heteroaryl which is unsubstituted or substituted;
Z is a bond or selected from the groups consisting of $C_{1-8}$alkylene, $NR^a$, $C(O)C_{1-8}$alkylene, $C_{1-8}$alkyleneNRa, $C_{1-6}$alkylenearylene$C_{1-6}$alkylene, $C_{2-8}$alkenylene, $C_{1-6}$alkylenearylene, $C_{1-6}$alkyleneheteroarylene, $C_{2-6}$alkenylenearylene$C_{1-6}$alkylene; any one of these groups being unsubstituted or substituted with one or more Ra;
M is selected from —NHOH, $CH_2SH$, $CH_2SC(O)C_{1-8}$alkyl, $CH_2SC(O)$aryl, $CH_2SC(O)$heteroaryl, $CH_2SC(O)C_{1-8}$alkylenearyl, $CH_2SC(O)C_{1-8}$alkylenheteroaryl or

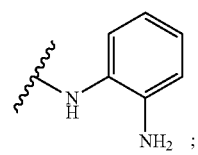

wherein

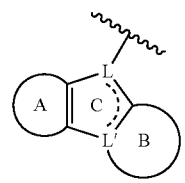

is selected from the following heterocyclic moieties:

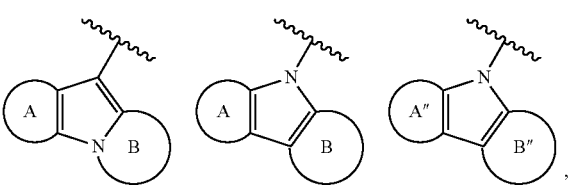

wherein

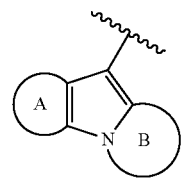

is selected from the following heterocyclic moieties:

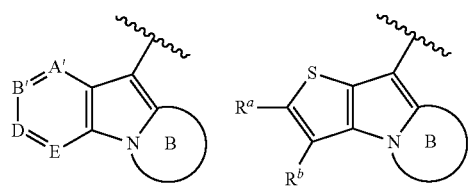

wherein each of A', B', D and E is independently selected from N, and $C(R^a)$;
wherein, in

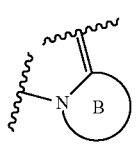

B ring is a 5 to 7-membered carbocyclic ring or a 5 to 7-membered carbocyclic ring in which one or more of the carbon atoms is replaced with C(O), O, S, $NR^c$,
wherein $R^c$ is selected from hydrogen, $C_1$-$C_6$alkyl, $C_1$-$C_6$cycloalkyl, $SO_2R^e$, $C(O)R^e$,
wherein $R^e$ is $C_1$-$C_6$alkyl, $C_1$-$C_6$cycloalkyl, aryl, heterocycle, heteroaryl, with the proviso that there are no N—O or N—S bonds in B ring;

wherein

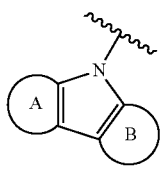

is selected from the following heterocyclic moieties:

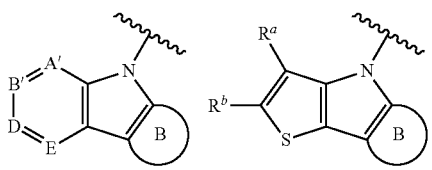

wherein each of A', B', D and E is independently selected from N, and C($R^a$) with the proviso that at least one of A', B', C and D is N, wherein

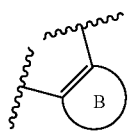

is a 5 to 7 membered carbocyclic ring or a 5 to 7 membered carbocyclic ring in which one or more of the carbon atoms is replaced with C(O), O, S, $NR^c$ wherein $R^c$ is selected from hydrogen, $C_1$-$C_6$alkyl, $C_1$-$C_6$cycloalkyl, aryl, heteroaryl, $C_1$-$C_6$alkylenearyl, $C_1$-$C_6$alkyleneheteroaryl, $SO_2R^e$, $C(O)R^e$, wherein $R^e$ is $C_1$-$C_6$alkyl, $C_1$-$C_6$cycloalkyl, aryl, heterocycle, heteroaryl, $C_1$-$C_6$alkylenearyl, $C_1$-$C_6$alkyleneheteroaryl;

wherein

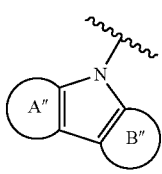

is selected from the following heterocyclic moieties:
wherein

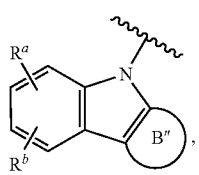

is selected from the following:

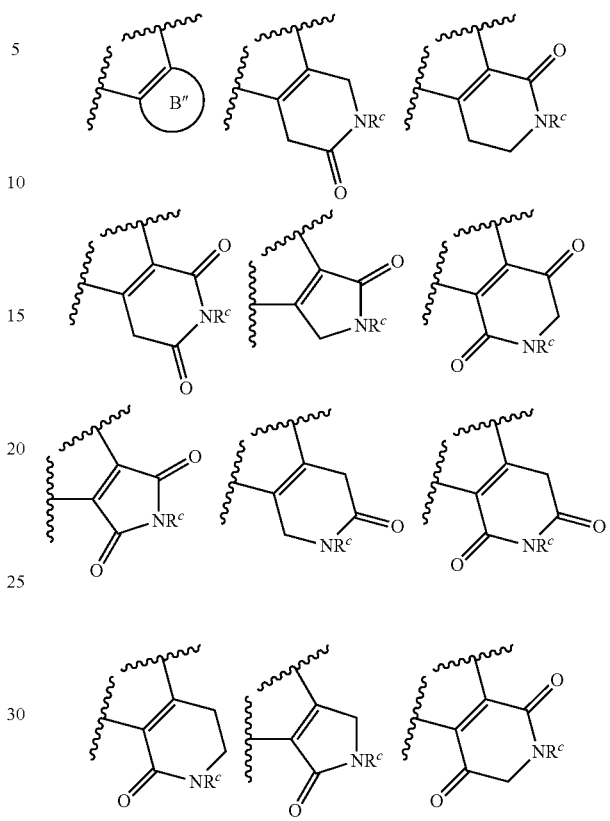

which are optionally substituted with one or more $R^a$ and $R^b$;

$R^a$ and $R^b$ are independently selected from hydrogen, aliphatic, alicyclic, heteroaliphatic, eterocyclic, aromatic, heteroaromatic, aryl, heteroaryl, alkylaryl, heteroalkylaryl, alkylheteroaryl, eteroalkylheteroaryl, alkoxy, aryloxy, heteroalkoxy, heteroaryloxy, alkylthio, arylthio, eteroalkylthio, heteroarylthio, F, Cl, Br, I, —OH, —$NO_2$, —CN, —$CF_3$, —$CH_2CF_3$, —$CHCl_2$, —$CH_2OH$, —$H_2CH_2OH$, —$CH_2NH_2$, —$CH_2SO_2CH_3$, —$C(O)R_x$, —$CO_2(R_x)$, —$CON(R_x)_2$, —$OC(O)R_x$, —$OCO_2R_x$, —$CON(R_x)_2$, —$N(R_x)_2$, —$SF_5$, —$S(O)R_x$, —$S(O)_2R_x$, —$NR_x(CO)R_x$, wherein each occurrence of $R_x$ independently includes aliphatic, alicyclic, heteroaliphatic, eterocyclic, aromatic, heteroaromatic, aryl, heteroaryl, alkylaryl, alkylheteroaryl, heteroalkylaryl r heteroalkylheteroaryl, wherein any one of the aliphatic, alicyclic, heteroaliphatic, heterocyclic, lkylaryl, or alkylheteroaryl substituents are substituted or unsubstituted, branched or unbranched, aturated or unsaturated, and wherein any one of the aromatic, heteroaromatic, aryl, heteroaryl, -alkyl)aryl or -(alkyl)heteroaryl substituents are substituted or unsubstituted;

wherein two adjacent $R^a$ or $R^a$ and $R^b$ can form a 5- to 7-membered carbocyclic ring or a 5- to 7-membered heterocyclic ring in which one or two carbon atoms are replaced by one or two S, O or $NR^c$.

2. A compound of claim 1 wherein M is —NHOH.

3. A compound of claim 2 wherein
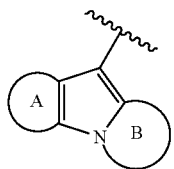
is selected from the following heterocyclic moieties:
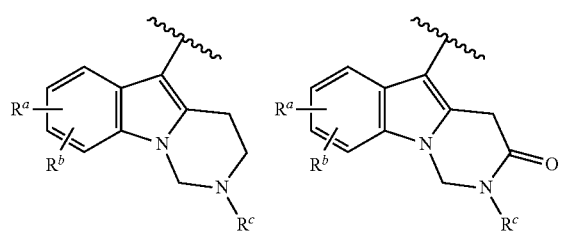
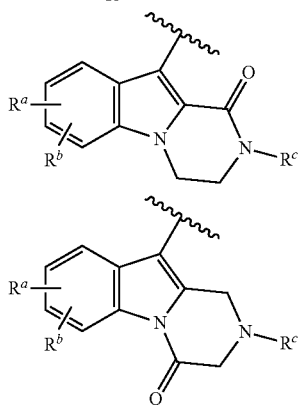
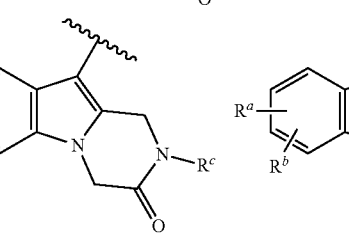
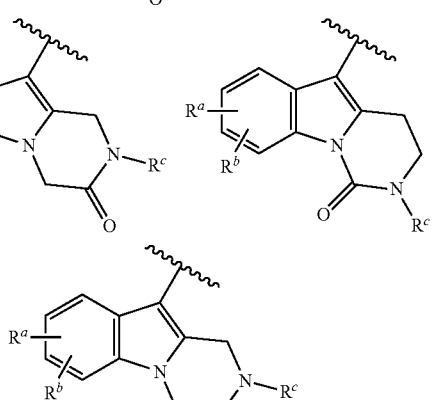
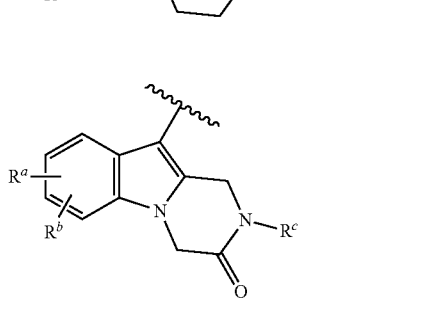
$R^a$, $R^b$ and $R^c$ are defined as in claim 1.
4. A compound of claim 2 wherein
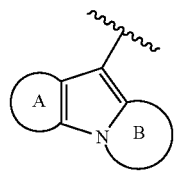
is selected from the following heterocyclic moieties:
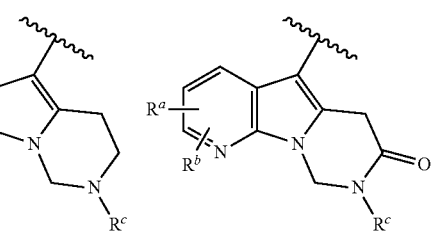
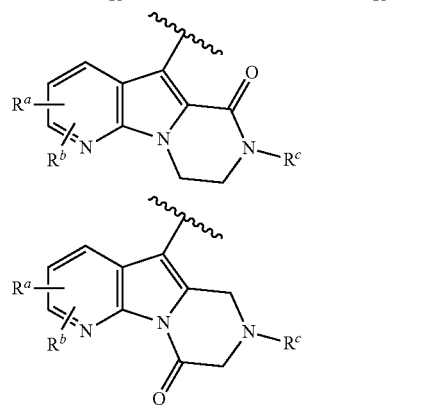
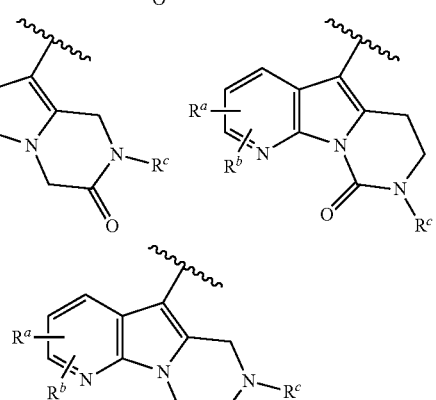
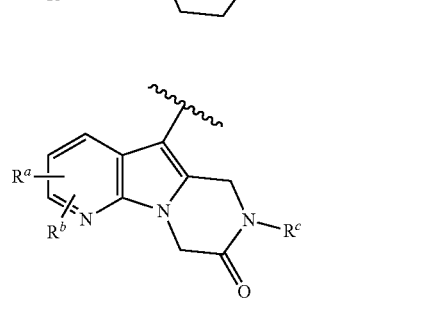
$R^a$, $R^b$ and $R^c$ are defined as in claim 1.

5. A compound of claim 2 wherein
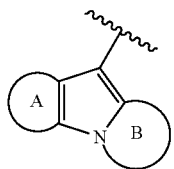
is selected from the following heterocyclic moieties:
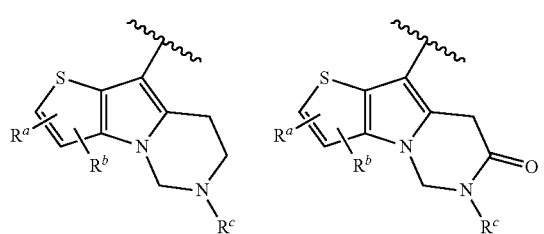
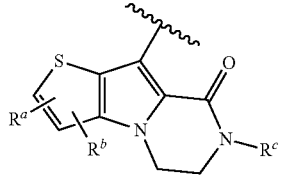
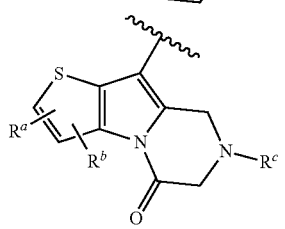
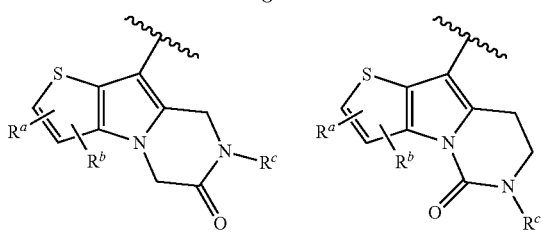
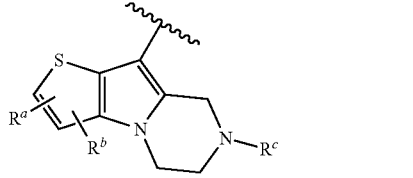
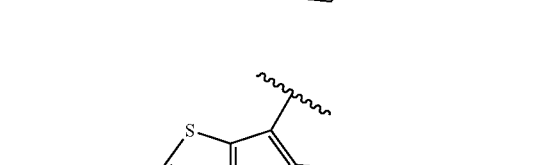
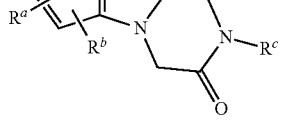
$R^a$, $R^b$ and $R^c$ are defined as in claim 1.
6. A compound of claim 1 wherein
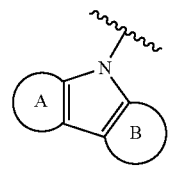
is selected from the following heterocyclic moieties:
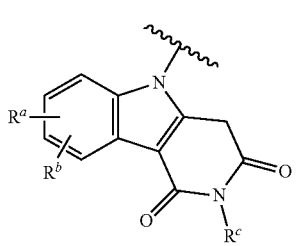
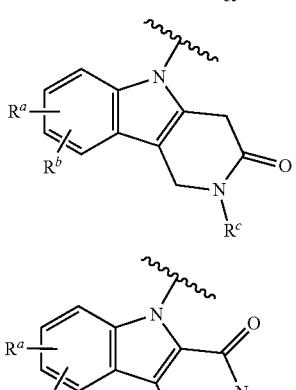
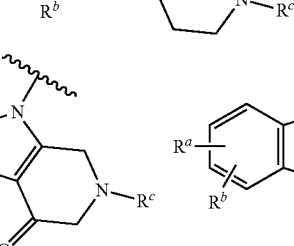
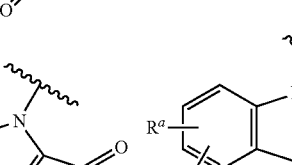

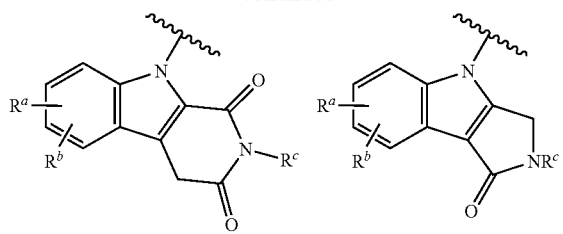

$R^a$, $R^b$ and $R^c$ are defined as in claim 1.

7. A compound of claim 2 wherein

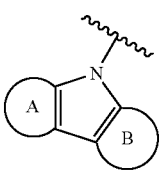

is selected from the following heterocyclic moieties:

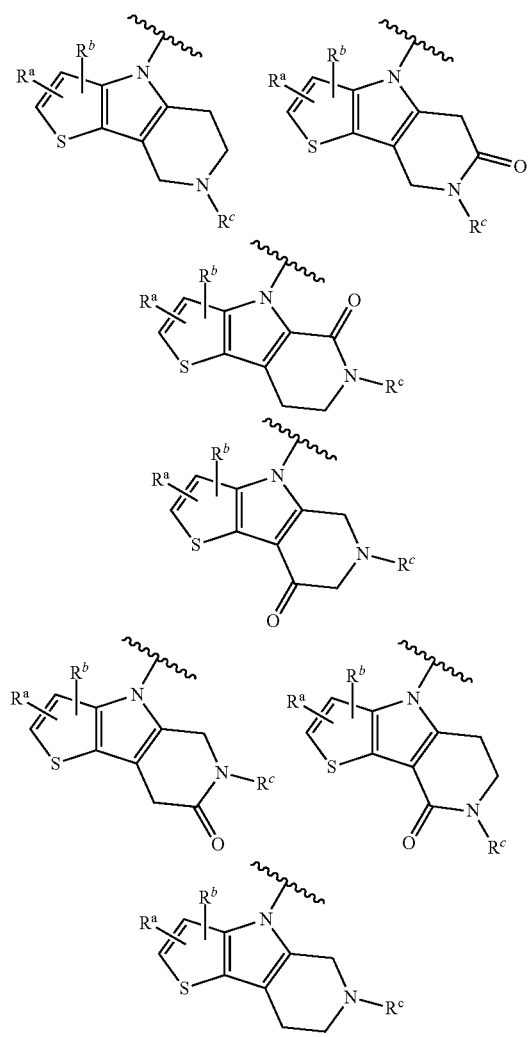

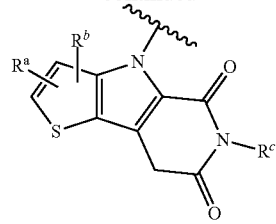

$R^a$, $R^b$ and $R^c$ are defined as in claim 1.

8. The compound of claim 1, wherein $R^a$ and $R^b$ are independently selected from H, $C_1$-$C_6$alkyl, $C_1$-$C_6$cycloalkyl, $CF_3$, $SF_5$, and halo.

9. A compound of claim 2 which is selected from the group consisting of:
 N-hydroxy-4-(2-methyl-1,2,3,4-tetrahydropyrimido[1,6-a]indol-5-ylthio)benzamide,
 4-(2,7-dimethyl-1,2,3,4-tetrahydropyrimido[1,6-a]indol-5-ylthio)-N-hydroxybenzamide,
 4-(2,8-dimethyl-1,2,3,4-tetrahydropyrimido[1,6-a]indol-5-ylthio)-N-hydroxybenzamide,
 4-(8-chloro-2-methyl-1,2,3,4-tetrahydropyrimido[1,6-a]indol-5-ylthio)-N-hydroxybenzamide,
 4-(8-fluoro-2-methyl-1,2,3,4-tetrahydropyrimido[1,6-a]indol-5-ylthio)-N-hydroxybenzamide
 4-(7-chloro-2-methyl-1,2,3,4-tetrahydropyrimido[1,6-a]indol-5-ylthio)-N-hydroxybenzamide
 4-(7-fluoro-2-methyl-1,2,3,4-tetrahydropyrimido[1,6-a]indol-5-ylthio)-N-hydroxybenzamide,
 N-hydroxy-4-(2-methyl-7-(trifluoromethyl)-1,2,3,4-tetrahydropyrimido[1,6-a]indol-5-ylthio)benzamide,
 N-hydroxy-4-(2-methyl-8-(trifluoromethyl)-1,2,3,4-tetrahydropyrimido[1,6-a]indol-5-ylthio)benzamide,
 N-hydroxy-4-[(8-methyl-6,7,8,9-tetrahydropyrido[3',2':4,5]pyrrolo[1,2-c]pyrimidin-5-yl)sulfanyl]benzamide,
 N-hydroxy-4-[(7-methyl-6,7,8,9-tetrahydropyrido[3',2':4,5]pyrrolo[1,2-a]pyrazin-5-yl)sulfanyl]benzamide,
 N-hydroxy-4-[(7-methyl-6-oxo-6,7,8,9-tetrahydropyrido[3',2':4,5]pyrrolo[1,2-a]pyrazin-5-yl)sulfanyl]benzamide,
 N-hydroxy-4-(2-methyl-1,2,3,4-tetrahydropyrazino[1,2-a]indol-10-ylthio)benzamide,
 4-(8-chloro-2-methyl-1,2,3,4-tetrahydropyrazino[1,2-a]indol-10-ylthio)-N-hydroxybenzamide,
 4-(8-fluoro-2-methyl-1,2,3,4-tetrahydropyrazino[1,2-a]indol-10-ylthio)-N-hydroxybenzamide,
 4-(2,8-dimethyl-1,2,3,4-tetrahydropyrazino[1,2-a]indol-10-ylthio)-N-hydroxybenzamide,
 4-(6-fluoro-2-methyl-1,2,3,4-tetrahydropyrazino[1,2-a]indol-10-ylthio)-N-hydroxybenzamide,
 4-(6-chloro-8-fluoro-2-methyl-1,2,3,4-tetrahydropyrazino[1,2-a]indol-10-ylthio)-N-hydroxybenzamide,
 4-(6,8-difluoro-2-methyl-1,2,3,4-tetrahydropyrazino[1,2-a]indol-10-ylthio)-N-hydroxybenzamide,
 4-(6,8-difluoro-2-methyl-1-oxo-1,2,3,4-tetrahydropyrazino[1,2-a]indol-10-ylthio)-N-hydroxybenzamide,
 4-(8-chloro-6-fluoro-2-methyl-1-oxo-1,2,3,4-tetrahydropyrazino[1,2-a]indol-10-ylthio)-N-hydroxybenzamide,
 4-(8-chloro-2-methyl-1-oxo-1,2,3,4-tetrahydropyrazino[1,2-a]indol-10-ylthio)-N-hydroxybenzamide,
 4-(8-fluoro-2-methyl-1-oxo-1,2,3,4-tetrahydropyrazino[1,2-a]indol-10-ylthio)-N-hydroxybenzamide,
 N-hydroxy-4-(2-methyl-1-oxo-1,2,3,4-tetrahydropyrazino[1,2-a]indol-10-ylthio)benzamide, N-hydroxy-4-((2-methyl-1-oxo-1,2,3,4-tetrahydropyrazino[1,2-a]indol-10-yl)methyl)benzamide,
4-((8-fluoro-2-methyl-1-oxo-1,2,3,4-tetrahydropyrazino[1,2-a]indol-10-yl)methyl)-N-hydroxybenzamide,
4-((6,8-difluoro-2-methyl-1-oxo-1,2,3,4-tetrahydropyrazino[1,2-a]indol-10-yl)methyl)-N-hydroxybenzamide,
4-((6,8-difluoro-2-methyl-1,2,3,4-tetrahydropyrazino[1,2-a]indol-10-yl)methyl)-N-hydroxybenzamide,
N-hydroxy-4-((2-methyl-1,2,3,4-tetrahydropyrazino[1,2-a]indol-10-yl)methyl)benzamide,
N-hydroxy-4-((2-methyl-1,2,3,4-tetrahydropyrimido[1,6-a]indol-5-yl)methyl)benzamide,
4-((7-fluoro-2-methyl-1,2,3,4-tetrahydropyrimido[1,6-a]indol-5-yl)methyl)-N-hydroxybenzamide,
4-((7-chloro-2-methyl-1,2,3,4-tetrahydropyrimido[1,6-a]indol-5-yl)methyl)-N-hydroxybenzamide,
4-((7-chloro-9-fluoro-2-methyl-1,2,3,4-tetrahydropyrimido[1,6-a]indol-5-yl)methyl)-N-hydroxybenzamide,
4-((7,9-difluoro-2-methyl-1,2,3,4-tetrahydropyrimido[1,6-a]indol-5-yl)methyl)-N-hydroxybenzamide,
4-(7,9-difluoro-2-methyl-1,2,3,4-tetrahydropyrimido[1,6-a]indole-5-carbonyl)-N-hydroxybenzamide,
N-hydroxy-4-(2-methyl-1,2,3,4-tetrahydropyrimido[1,6-a]indole-5-carbonyl)benzamide,
N-hydroxy-4-[(7-methyl-6-oxo-6,7,8,9-tetrahydropyrido[3',2':4,5]pyrrolo[1,2-a]pyrazin-5-yl)methyl]benzamide,
N-hydroxy-4-[(7-methyl-6,7,8,9-tetrahydropyrido[3',2':4,5]pyrrolo[1,2-a]pyrazin-5-yl)methyl]benzamide,
N-hydroxy-4-[(8-methyl-6,7,8,9-tetrahydropyrido[3',2':4,5]pyrrolo[1,2-c]pyrimidin-5-yl)methyl]benzamide,
N-hydroxy-4-[(6-methyl-5,6,7,8-tetrahydrothieno[2',3':4,5]pyrrolo[1,2-c]pyrimidin-9-yl)methyl]benzamide,
4-[(2,6-dimethyl-5,6,7,8-tetrahydrothieno[2',3':4,5]pyrrolo[1,2-c]pyrimidin-9-yl)methyl]-N-hydroxybenzamide,
4-[(2,6-dimethyl-5,6,7,8-tetrahydrothieno[2',3':4,5]pyrrolo[1,2-c]pyrimidin-9-yl)sulfanyl]-N-hydroxybenzamide,
4-[(2,7-dimethyl-5,6,7,8-tetrahydrothieno[2',3':4,5]pyrrolo[1,2-a]pyrazin-9-yl)sulfanyl]-N-hydroxybenzamide,
4-[(2,7-dimethyl-8-oxo-5,6,7,8-tetrahydrothieno[2',3':4,5]pyrrolo[1,2-a]pyrazin-9-yl)sulfanyl]-N-hydroxybenzamide,
N-hydroxy-4-[(7-methyl-8-oxo-5,6,7,8-tetrahydrothieno[2',3':4,5]pyrrolo[1,2-a]pyrazin-9-yl)sulfanyl]benzamide,
N-hydroxy-4-[(7-methyl-5,6,7,8-tetrahydrothieno[2',3':4,5]pyrrolo[1,2-a]pyrazin-9-yl)methyl]benzamide,
N-hydroxy-4-[(7-methyl-8-oxo-5,6,7,8-tetrahydrothieno[2',3':4,5]pyrrolo[1,2-a]pyrazin-9-yl)methyl]benzamide,
4-[(2,7-dimethyl-8-oxo-5,6,7,8-tetrahydrothieno[2',3':4,5]pyrrolo[1,2-a]pyrazin-9-yl)methyl]-N-hydroxybenzamide,
4-(2,8-dimethyl-1-oxo-1,2,3,4-tetrahydropyrazino[1,2-a]indol-10-ylthio)-N-hydroxybenzamide,
N-hydroxy-4-[(7-methyl-5,6,7,8-tetrahydro-4H-thieno[2',3':4,5]pyrrolo[3,2-c]pyridin-4-yl)methyl]benzamide,
4-[(2,7-dimethyl-5,6,7,8-tetrahydro-4H-thieno[2',3':4,5]pyrrolo[3,2-c]pyridin-4-yl)methyl]-N-hydroxybenzamide,
4-[(2,7-dimethyl-6-oxo-5,6,7,8-tetrahydro-4H-thieno[2',3':4,5]pyrrolo[3,2-c]pyridin-4-yl)methyl]-N-hydroxybenzamide,
4-[(2,7-dimethyl-8-oxo-5,6,7,8-tetrahydro-4H-thieno[2',3':4,5]pyrrolo[3,2-c]pyridin-4-yl)methyl]-N-hydroxybenzamide,
N-hydroxy-4-[(6-methyl-5-oxo-5,6,7,8-tetrahydro-9H-pyrido[3',4':4,5]pyrrolo[2,3-b]pyridin-9-yl)methyl]benzamide,
N-hydroxy-4-[(6-methyl-5,6,7,8-tetrahydro-9H-pyrido[3',4':4,5]pyrrolo[2,3-b]pyridin-9-yl)methyl]benzamide,
N-hydroxy-4-[(6-methyl-7-oxo-5,6,7,8-tetrahydro-9H-pyrido[3',4':4,5]pyrrolo[2,3-b]pyridin-9-yl)methyl]benzamide,
N-hydroxy-4-[(7-methyl-5,6,7,8-tetrahydro-9H-pyrido[4',3':4,5]pyrrolo[2,3-b]pyridin-9-yl)methyl]benzamide,
N-hydroxy-4-[(7-methyl-6-oxo-5,6,7,8-tetrahydro-9H-pyrido[4',3':4,5]pyrrolo[2,3-b]pyridin-9-yl)methyl]benzamide,
N-hydroxy-4-[(6-methyl-7-oxo-5,6,7,8-tetrahydro-4H-thieno[2',3':4,5]pyrrolo[2,3-c]pyridin-4-yl)methyl]benzamide,
4-[(2,6-dimethyl-7-oxo-5,6,7,8-tetrahydro-4H-thieno[2',3':4,5]pyrrolo[2,3-c]pyridin-4-yl)methyl]-N-hydroxybenzamide,
4-[(2,6-dimethyl-5,6,7,8-tetrahydro-4H-thieno[2',3':4,5]pyrrolo[2,3-c]pyridin-4-yl)methyl]-N-hydroxybenzamide,
4-[(2,6-dimethyl-5-oxo-5,6,7,8-tetrahydro-4H-thieno[2',3': 4,5]pyrrolo[2,3-c]pyridin-4-yl)methyl]-N-hydroxybenzamide,
N-hydroxy-4-((2-methyl-3-oxo-3,4-dihydro-1H-pyrido[3,4-b]indol-9(2H)-yl)methyl)benzamide,
N-hydroxy-4-((2-methyl-1-oxo-3,4-dihydro-1H-pyrido[3,4-b]indol-9(2H)-yl)methyl)benzamide,
N-hydroxy-4-((2-methyl-3-oxo-3,4-dihydro-1H-pyrido[4,3-b]indol-5 (2H)-yl)methyl)benzamide,
N-hydroxy-4-((2-methyl-1,3-dioxo-3,4-dihydro-1H-pyrido[4,3-b]indol-5 (2H)-yl)methyl)benzamide, and
N-hydroxy-4-((2-methyl-1-oxo-3,4-dihydro-1H-pyrido[4,3-b]indol-5 (2H)-yl)methyl)benzamide.

10. A pharmaceutical composition comprising a combination of a compound of claim 1 and a second anti-cancer agent selected from a cytotoxic agent, a antimitotic agent, an antimetabolite, a proteasome inhibitor, a monoclonal antibody, a kinase inhibitor and a pharmaceutically acceptable carrier.

11. A pharmaceutical composition comprising a compound of claim 1 and a pharmaceutically acceptable carrier.

* * * * *